US008426203B2

(12) United States Patent
Thomson et al.

(10) Patent No.: US 8,426,203 B2
(45) Date of Patent: *Apr. 23, 2013

(54) CULTURE MEDIUM CONTAINING GAMMA-AMINOBUTYRIC ACID, PIPECOLIC ACID OR LITHIUM FOR THE MAINTENANCE OF STEM CELLS IN AN UNDIFFERENTIATED STATE

(75) Inventors: James A. Thomson, Madison, WI (US); Tenneille Ludwig, Fitchburg, WI (US)

(73) Assignee: Wisconsin Alumni Research Foundation, Madison, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/427,548

(22) Filed: Mar. 22, 2012

(65) Prior Publication Data

US 2012/0178161 A1     Jul. 12, 2012

Related U.S. Application Data

(63) Continuation of application No. 12/754,574, filed on Apr. 5, 2010, now Pat. No. 8,158,424, which is a continuation-in-part of application No. 12/209,325, filed on Sep. 12, 2008, now abandoned, which is a continuation of application No. 11/221,457, filed on Sep. 8, 2005, now Pat. No. 7,449,334, said application No. 12/754,574 is a continuation-in-part of application No. 12/242,085, filed on Sep. 30, 2008, now abandoned, which is a continuation of application No. 11/221,516, filed on Sep. 8, 2005, now Pat. No. 7,442,548.

(60) Provisional application No. 60/608,040, filed on Sep. 8, 2004, provisional application No. 60/695,100, filed on Jun. 29, 2005.

(51) Int. Cl.
*C12N 5/04* (2006.01)

(52) U.S. Cl.
USPC ............ 435/404; 435/405; 435/406; 435/407

(58) Field of Classification Search .................. None
See application file for complete search history.

(56) References Cited

U.S. PATENT DOCUMENTS

| | | | |
|---|---|---|---|
| 6,800,480 B1 | 10/2004 | Bodnar et al. | |
| 7,005,252 B1 | 2/2006 | Thomson et al. | |
| 7,217,569 B2 | 5/2007 | Thomson et al. | |
| 7,297,539 B2 | 11/2007 | Mandalam et al. | |
| 7,410,798 B2 | 8/2008 | Mandalam et al. | |
| 7,413,902 B2 | 8/2008 | Bodnar et al. | |
| 7,442,548 B2* | 10/2008 | Thomson et al. | 435/366 |
| 7,449,334 B2* | 11/2008 | Thomson et al. | 435/377 |
| 7,455,983 B2 | 11/2008 | Xu et al. | |
| 7,592,175 B2 | 9/2009 | Amit et al. | |
| 8,158,424 B2* | 4/2012 | Thomson et al. | 435/377 |
| 2006/0014279 A1 | 1/2006 | Xu et al. | |

FOREIGN PATENT DOCUMENTS

| | | |
|---|---|---|
| WO | 03020920 A1 | 3/2003 |
| WO | 2004055155 A2 | 7/2004 |
| WO | 2005068615 Z1 | 7/2005 |

OTHER PUBLICATIONS

Am It et al., Feeder Layer- and Serum-Free Culture of Human Embryonic Stem Cells, Biology of reproduction 70:837-845 (2004).
Aubert et al., "Functional gene screening in embryonic stem cells implicates Wnt antagonism in neural differentiation," Nature Biotechnology 20:1240-1245 (2002).
BD Matrigel Basement Membrane Matrix and BD Matrigel Basement Membrane matrix High Concentration (HC), BD Biosciences Online XP-022369813.
Carpenter et al., "Properties of four human embryonic stem cell lines maintained in a feeder-free culture system," Developmental Dynamics 229:243-258 (2004).
Evans et al., "Establishment in culture of pluripotential cells from mouse embryos", Nature 292:154-156 (1981).
Klimanskaya et al., "Human embryonic stem cells derived without feeder cells", The Lancet 365:1636-1641 (2005).
Li et al., "Expansion of Human Embryonic Stem Cells in Defined Serum-Free Medium Devoid of Animal-Derived .." Biotechnology and Bioengineering 91; 688,698 (2005).
Mayazono "Positive and negative regulation ofTGF-B signaling", Journal of Cell Science 113:1101-1109 (2000).
Park et al., "Wnt activation accompanied not with maintenance of pluripotency but with differentiation of human.." Anatomical Science International 79:337 (2004).
Reya et al., "A role for Wnt signalling in self-renewal of haematopoietic stem cells",Nature 423:409-414 (2003).
Schmidt et al., "Lithium influences differentiation and tissue-specific gene expression of mouse embryonic stem (ES) cells in vitro" Int. J. Dev. Bioi. 45:421-429 (2001).

(Continued)

*Primary Examiner* — Deborah Crouch
(74) *Attorney, Agent, or Firm* — Quarles & Brady LLP

(57) ABSTRACT

Previous methods for culturing primate pluripotent stem cells have required either fibroblast feeder cells or a medium which was exposed to fibroblast feeder cells to maintain the stem cells in an undifferentiated state. It has now been found that high levels of fibroblast growth factor in a medium together with at least one of gamma aminobutyric acid, pipecolic acid, and lithium, enables pluripotent stem cells to remain undifferentiated indefinitely through multiple passages, even without feeder cells or conditioned medium. Without beta-mercaptoethanol, the medium improves cloning efficiency. Also, a matrix of human proteins can be used to culture the undifferentiated cells without exposing the cells to animal products. Further disclosed are new primate pluripotent cell lines made using the defined culture conditions, including the medium and the matrix. Such new cell lines will have never been exposed to animal cells, animal products, feeder cells or conditioned medium.

5 Claims, 23 Drawing Sheets

OTHER PUBLICATIONS

Solter et al., "Immunosurgery of mouse blastocyst", Proc. Nat. Acad. Sci. USA 72: 5099-5102 (1975).

Xu et al., "Basic FGF and suppression of BMP signaling sustain undifferentiated proliferation of human ES cells," Nature Methods. 2:185-190 (2005).

Xu et al., Feeder-Free Growth of Undifferentiated Human Embryonic Stem Cells, Nature Biotechnology, vol. 19, pp. 971-974.

Ying et al., BMP Induction of Id Proteins Suppresses Differentiation and Sustains Embryonic Stem Cell Self-Renewal in Collaboration with STAT3, • Cell115:281-292 (2003).

Ludwig et al., Derivation of human embryonic stem cells in defined conditions, Nature Biotechnology 24, 185-187 (2006).

Ludwig et al., Feeder-independent culture of human embryonic stem cells Nature Methods, 3, 637-646 (2006).

Yu et al., Induced Pluripotent Stem Cell Lines Derived from Human Somatic Cells, Science, vol. 318, pp. 1917-1920 (2007).

Chan et al., Live cell imaging distinguishes bona fide human iPS cells from partially reprogrammed cells, Nature, vol. 27, pp. 1033-1037.

Sun et al., Feeder-free derivation of induced pluripotent stem cells from adult human adipose stem cells, PNAS 106 (37), 1570-15725 (2009).

* cited by examiner

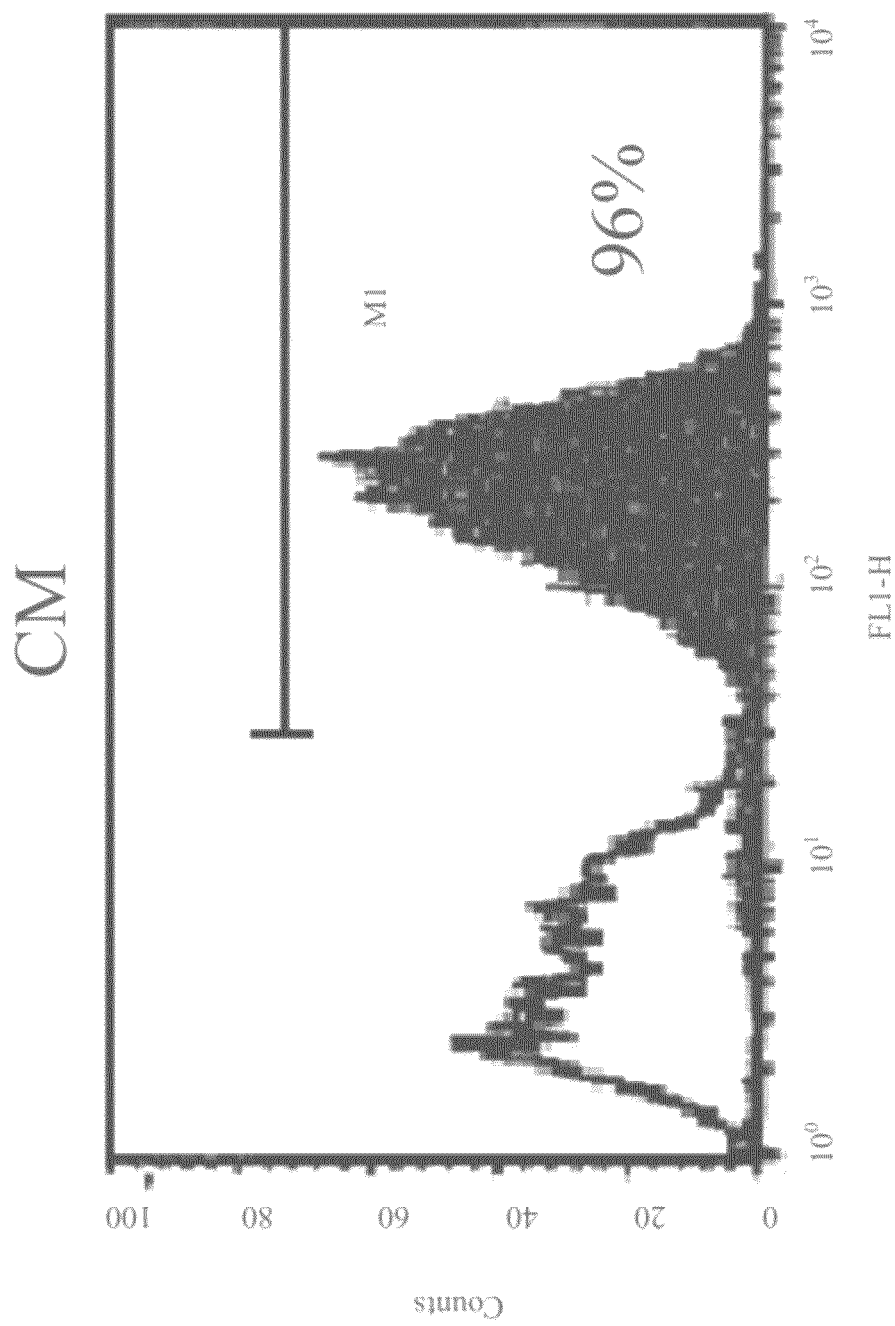

A.

B.

CULTURE MEDIUM CONTAINING GAMMA-AMINOBUTYRIC ACID, PIPECOLIC ACID OR LITHIUM FOR THE MAINTENANCE OF STEM CELLS IN AN UNDIFFERENTIATED STATE

CROSS-REFERENCE TO RELATED APPLICATIONS

This application is a continuation of U.S. Application Ser. No. 12/754,574 filed on Apr. 5, 2010. U.S. Application Ser. No. 12/754,574 is a continuation-in-part of U.S. Application Ser. No. 12/209,325 filed Sep. 12, 2008, which is a continuation of U.S. Application Ser. No. 11/221,457, filed Sep. 8, 2005, now U.S. Pat. No. 7,449,334 issued Nov. 11, 2008, which claimed priority from U.S. provisional patent application Ser. No. 60/608,040 filed Sep. 8, 2004. Also, U.S. application Ser. No. 12/754,574 is a continuation-in-part of U.S. application Ser. No. 12/242,085 filed Sep. 30, 2008, which is a continuation of U.S. application Ser. No. 11/221,516 filed Sep. 8, 2005, now U.S. Pat. No. 7,442,548 issued Oct. 28, 2008, which claimed priority from U.S. provisional patent application Ser. No. 60/695,100 filed Jun. 29, 2005. Therefore, U.S. application Ser. No. 12/754,574 claimed priority from both U.S. provisional patent application Ser. Nos. 60/608,040 and 60/695,100. Each of the above listed applications is incorporated herein by reference in its entirety.

STATEMENT REGARDING FEDERALLY SPONSORED RESEARCH OR DEVELOPMENT

Some of the work described in this specification was supported by grants from the U.S. Government and some was not. None of the work described in this specification on the process of deriving new human embryonic stem cell lines was supported by any grant money from the United States government. New human embryonic stem cell derivations and analyses were performed exclusively at WiCell, using privately funded WiCell facilities, equipment and personnel. To the extent this invention was made with United States government support, the award was provided by: NIH R24-RR017721 and P20-GMO69981. The government has certain rights in the invention.

BACKGROUND OF THE INVENTION

Primate embryonic stem (ES) cells and the recently-described induced pluripotent stem cells (iPS) (collectively, "pluripotent cells") can proliferate without limit and can differentiate into each of the three embryonic germ layers. ES cells are stem cells found in or derived from embryos. ES cells are capable of differentiation into most, if not all, of the differentiated cell types of a mature body. It is understood that iPS cells behave in culture essentially the same as ES cells. iPS cells and ES cells express one or more pluripotent cell-specific marker, such as Oct-4, SSEA-3, SSEA-4, Tra 1-60, Tra 1-81, and Nanog (Yu et al. *Science*, Vol. 318. no. 5858, pp. 1917-1920 (2007), incorporated by reference here in its entirety) Also, recent findings of Chan, suggest that expression of Tra 1-60, DNMT3B, and REX1 can be used to positively identify fully reprogrammed iPS cells, whereas alkaline phosphatase, SSEA-4, GDF3, hTERT, and NANOG are insufficient as markers of fully reprogrammed iPS cells. (Chan et al., *Nat. Biotech.* 27:1033-1037 (2009), incorporated by reference here in its entirety). Subsequent references herein to primate or human ES cells and the like are intended to apply with equal force to iPS cells.

Pluripotent cells are of high interest to the research community and regenerative industry because they are capable of indefinite proliferation in culture. Thus, at least in principle, pluripotent cells are capable of supplying cells and tissues for replacement of failing or defective human tissue. This is why the existence of human pluripotent stem cells in culture offers the potential of unlimited amounts of human cells and tissues for use in a variety of therapeutic protocols to assist in human health. It is envisioned in the future that human pluripotent stem cells will be proliferated and directed to differentiate into specific lineages so as to develop differentiated cells or tissues which can be transplanted into human bodies for therapeutic purposes. Human pluripotent stem cells and the differentiated cells that may be derived from them are also powerful scientific tools for the study of human cellular and developmental systems.

Specifically, the basic techniques to create and culture human ES cells have been described. The previously reported techniques do work, but there are limitations and drawbacks to many of the procedures currently used to culture human ES cells. One limitation of particular concern is that most existing human ES cell lines have been, to one degree or another, exposed directly to mouse cells or to a medium in which mouse cells have been previously cultured. This is because the original techniques for generating and culturing human ES cells required using mouse embryonic fibroblast (MEF) feeder cells as a feeder layer on which human ES cells could be cultured. The fibroblast feeder cells act, through some as yet incompletely understood mechanism, to encourage the stem cells to remain in an undifferentiated state. A by-product of such techniques is that some human ES cells from existing cell lines were found to exhibit the sialic residue Neu5Gc, which is not normally made by human cells but is made by murine cells, and has received much attention in the press.

Later, it was discovered that the benefits MEF feeder cells provide to stem cells grown in culture could be obtained by exposing stem cells to "conditioned medium." Conditioned medium is a stem cell culture medium in which feeder cells, such as MEFs, had been previously cultured. In conditioned medium, either the feeder cells impart some factor to the medium or remove some factor from the medium, which allows stem cells to be cultured in an undifferentiated state. Although the mechanisms involved in the beneficial effects of conditioned medium have not been fully elucidated, the result is that conditioned medium can be used to maintain stem cells in culture with minimal differentiation. Both direct growth of human pluripotent stem cells on murine feeder cells and the use of conditioned media raise the concern that one or more agents, such as a virus, could be transmitted from the mouse cells to the human pluripotent stem cells. If one of the applied objectives of human pluripotent stem cell cultures is to create cells and tissues which can ultimately be transplanted into a human body, it is highly desirable to generate stem cells that have never been exposed to cells of another species or to media which have been used to culture cells of another species. Accordingly, defining a culture condition, which will permit the proliferation and culture of human pluripotent stem cells without a fibroblast feeder layer, is of great interest in the continued development of techniques for the long term culture of human pluripotent stem cells.

Several medium formulations will permit human pluripotent stem cells to remain undifferentiated for some time, but the undifferentiated state often fails to maintain itself. The inventors here have found several medium formulations that permit the cultivation of human pluripotent stem cells for one or two passages without severe differentiation, but then the cells differentiate rapidly upon subsequent passages. In particular, "passage" is defined herein as the growth of human pluripotent stem cells from an initial seed culture in a culture vessel to confluence in the same culture vessel. The inventors have come to believe that in order for a culture medium to truly support the indefinite proliferation of human pluripotent stem cells without differentiation and without fibroblast feeder cells or medium that is conditioned therewith, the medium must be capable of supporting culture of human pluripotent stem cells in a substantially uniform and undifferentiated state for at least five passages. It is also important that the cultures remain relatively homogenous and undifferentiated throughout the culture period and retain all of the important characteristics of human pluripotent stem cells.

A characteristic trait of human pluripotent stem cells in culture is that, if conditions are less than ideal, the cells have a tendency to differentiate. It is easy to induce human pluripotent stem cells to differentiate, while it is challenging to maintain human pluripotent stem cells in an undifferentiated state in culture. Most culture conditions will result in some level of unwanted differentiation, particularly around the periphery of the growing pluripotent stem cell colony. While pluripotent stem cells can be cultured with some degree of unwanted differentiation, the objective is to define a culture condition that permits the culture to remain as undifferentiated as possible, i.e., with as few differentiated cells as possible. To achieve this objective, the inventors have used particularly stringent standards to define conditions that will support the indefinite culture of undifferentiated pluripotent stem cell cultures, as described below.

The state of differentiation of a stem cell culture can be assessed by morphological characteristics. Undifferentiated stem cells have a characteristic morphology, i.e., small and compact cells with clearly defined cell borders, a morphology which can be easily seen by examination of a stem cell culture under a microscope. By contrast, cells which have differentiated appear larger and more diffuse with indistinct cell borders. While some differentiated cells can, and normally do, appear at the margin of colonies of undifferentiated cells, the optimal stem cell culture is one that proliferates in the culture vessel with only minimal numbers of cells at the periphery of the culture appearing to be differentiated. With experience, stem cell researchers can judge the status of differentiation and health of human pluripotent stem cell cultures visually with good accuracy.

In addition to morphological characteristics, biochemical cell markers are routinely used to track the status of ES cells as undifferentiated. For example, transcription factor Oct-4 is regarded as the most reliable marker of undifferentiated status for ES cells. Oct-4 is also one of the first markers lost as undifferentiated cells begin to differentiate. Other biochemical markers used to track the status of undifferentiated primate ES cells and human ES cells include: SSEA-3, SSEA-4, Tra 1-60, and Tra 1-81 and alkaline phosphatase, but not SSEA-1. In contrast, undifferentiated mouse ES cells express SSEA-1, but not SSEA-3, SSEA-4, Tra 1-60, and Tra 1-81. Tra 1-60, and Tra 1-81 are antibodies to extracellular matrix molecules synthesized by undifferentiated pluripotent stem cells, which are also markers for human ES cells. Further, it has been shown that Nanog is a transcription factor that is essential for the maintenance of pluripotency and self renewal in pluripotent stem cells.

In addition to stringent standards required for conditions that will support the indefinite culture of undifferentiated pluripotent stem cell cultures, the conditions needed for derivation of new lines of human pluripotent stem cells is an even more stringent. This is because some culture conditions which support the expansion and growth of existing stem cells lines have not proven sufficient for use in the derivation of new human pluripotent stem cell lines. It appears that the capacity to support the initiation of new lines of stem cells is a capacity that not all stem cell culture conditions feature. Accordingly, media to support initiation, proliferation and culture of undifferentiated primate stem cells are desired by the stem cell industry.

BRIEF SUMMARY OF THE INVENTION

In a first aspect, the invention is summarized as a defined medium for culturing primate pluripotent stem cells, including ES cells and iPS cells. The medium is a serum-free, animal product-free medium that supports the derivation and long-term feeder-independent culture of primate pluripotent stem cells. The defined medium includes salts, vitamins, amino acids, glucose, lipids, a fibroblast growth factor (FGF), and at least one of gamma amino butyric acid (GABA), pipecolic acid (PA), and lithium (Li), all in sufficient amount to maintain the stem cells in an undifferentiated state through multiple culture passages. Optionally, transforming growth factor beta (TGFβ) may be added to the defined medium in sufficient amount so the stem cells can be cultured indefinitely in an undifferentiated, pluripotent and proliferative state without the need for fibroblast feeder cells or conditioned medium.

Another aspect of the invention provides a method for culturing primate pluripotent stem cells on a matrix with a defined medium without the need for feeder cells or conditioned medium to maintain the stem cells in an undifferentiated state through multiple successive culture passages. The method includes the step of culturing pluripotent stem cells in a medium including salts, vitamins, amino acids, glucose, lipids, a FGF, and at least one of GABA, PA, and Li, all in sufficient amount to maintain the stem cells in an undifferentiated state through multiple culture passages.

Another aspect of the present invention is directed to an in vitro cell culture of primate pluripotent stem cells cultured in a medium including high levels of a FGF, lipids and at least one of GABA, PA, and Li, so that the stem cells can be cultured indefinitely in an undifferentiated state without the need for fibroblast feeder cells or conditioned medium.

The present invention also provides a method for the creation and maintenance of new primate pluripotent stem cell lines, which can be cultured in an undifferentiated state, and which have not been exposed to animal products, feeder cells, or conditioned medium. Also disclosed are defined long term culture conditions for human pluripotent stem cells that avoid exposure to and the use of animal cells or proteins in which stem cells are often cultured.

Another aspect of the invention provides a method for culturing human pluripotent stem cells on a matrix in a medium without feeder cells or conditioned media, the medium including salts, vitamins, amino acids, glucose, albumin, minerals, lipids, a transferrin or a transferrin substitute, insulin or an insulin substitute, a FGF, and at least one member selected from GABA, PA and Li, in sufficient amounts to maintain the cells in an undifferentiated state through multiple successive culture passages. A suitable matrix is a solubilized basement membrane preparation extracted from the Engelbreth-Holm-Swarm mouse sarcoma (Matrigel™) or a matrix that includes human matrix proteins collagen IV and at least one member selected from fibronectin, laminin and vitronectin. Preferably, collagen IV, fibronectin, laminin and vitronectin are all included in the matrix. Optionally, TGFβ may be added to the defined medium. The defined growth factors, GABA, PA and Li, are added in sufficient amounts to maintain the human stem cells in an undifferentiated state, wherein at least 90% of the cells in culture are positive for the transcription factor Oct-4 through multiple successive culture passages.

Another aspect of the invention provides an in vitro cell culture having in a culture vessel: primate pluripotent stem cells; a matrix, on which the stem cells can grow; and a culture medium, wherein the medium comprises salts, vitamins, amino acids, glucose, albumin, minerals, lipids, a transferrin or a transferrin substitute, insulin or an insulin substitute, a FGF, and at least one member selected from GABA, PA, and Li, in sufficient amounts to maintain the human stem cells in an undifferentiated state through multiple culture passages, the medium being free of feeder cells and never having been exposed to feeder cells.

In a related aspect, the matrix includes at least one of collagen IV, fibronectin, laminin, and vitronectin. Preferably, at least two, more preferably at least three, and most preferably all four human matrix proteins are present. The culture medium includes salts, vitamins, amino acids, glucose, albumin, minerals, lipids, a transferrin or a transferrin substitute, insulin or an insulin substitute, a FGF, GABA, PA, Li and transforming growth factor beta in sufficient amounts to maintain the human stem cells in an undifferentiated state, so that at least 90% of the cells in culture are positive for the transcription factor Oct-4 through multiple culture passages, the medium being free of feeder cells and never having been exposed to feeder cells. Preferably, the medium also is free of products from non-human animals.

In another aspect, the invention provides a medium comprising salts, vitamins, amino acids, glucose, albumin, minerals, lipids, a transferrin or a transferrin substitute, insulin or an insulin substitute, a FGF, and at least one member selected from GABA, PA, and Li, and optionally TGFβ in sufficient amounts to maintain stem cells grown in the medium in an undifferentiated state through multiple culture passages, wherein at least 90% of the cells in culture are positive for the transcription factor Oct-4 through multiple culture passages. Suitably, the FGF concentration is at least between 40 ng/ml and 100 ng/ml. In a related aspect, when beta-mercaptoethanol was either omitted or added at a concentration less than about 0.1 mM in the culture medium, cloning efficiency of the pluripotent stem cells increased by at least 10% compared to pluripotent stem cells cultured in the same medium, having a higher than about 0.1 mM concentration of beta-mercaptoethanol.

Another aspect of the invention provides a method for initiating a cultured line of primate pluripotent stem cells without the use of feeder cells or conditioned medium, the method including the step of plating cells from a blastocyst onto a matrix in a medium including salts, vitamins, amino acids, glucose, albumin, minerals, lipids, a transferrin or a transferrin substitute, insulin or an insulin substitute, a FGF and at least one member selected from GABA, PA, and Li, in sufficient amounts to originate and maintain a new proliferating stem cell line in an undifferentiated state.

Another aspect provides a method of culturing new primate pluripotent stem cells including the steps of culturing stem cells that have been isolated from the inner cell mass of an embryo in the blastocyst stage in a medium including salts, vitamins, amino acids, glucose, albumin, minerals, lipids, a transferrin or a transferrin substitute, insulin or an insulin substitute, a FGF, and at least one of GABA, PA, and Li, in sufficient amounts to maintain the stem cells in an undifferentiated state through multiple culture passages, the culturing step being conducted on a matrix of human proteins comprising collagen and at least one protein selected from fibronectin, vitronectin, and laminin, the medium being free of feeder cells and never having been exposed to feeder cells; and serially expanding the cells which proliferate on the medium.

Another aspect of the invention provides a culture of human pluripotent stem cells having (i) human pluripotent stem cells on a matrix of human proteins that comprises a humanized matrix made from human collagen and at least one human protein selected from fibronectin, vitronectin and laminin and (ii) a cell culture medium that comprises salts, vitamins, amino acids, glucose, albumin, minerals, lipids, a transferrin or a transferrin substitute, insulin or an insulin substitute, a FGF and at least one member selected from GABA, PA, and Li, the medium being free of feeder cells and never having been exposed to feeder cells. In a related aspect, the matrix includes collagen, fibronectin, vitronectin and laminin. Also included are GABA, PA, and Li. In this aspect, the cultured pluripotent cells are human embryonic stem cells, which do not exhibit the sialic acid Neu5Gc and the medium is capable of maintaining the cells through over twenty passages in culture while the cells remain undifferentiated, maintain pluripotency, and maintain stable karyotype.

Another aspect of the invention is a cell culture medium having albumin, minerals, vitamins, amino acids, glucose, a FGF, lipids, a transferrin or a transferrin substitute, insulin or an insulin substitute, and at least two members selected from GABA, PA, and Li in sufficient amounts to maintain cells in an undifferentiated state through multiple culture passages, wherein the medium is free of feeder cells and never having been exposed to feeder cells.

Another aspect of the invention is that with the medium and culture system described here, one can establish and maintain primate pluripotent stem cell lines that comprise at least 70%, at least 80%, more preferably at least 85%, and most preferably at least 90% undifferentiated stem cells.

Another aspect of the invention is a method of increasing cloning efficiency of primate pluripotent stem cells by culturing the primate pluripotent stem cells on a matrix in a medium without feeder cells or conditioned media, the medium comprising salts, vitamins, amino acids, glucose, albumin, minerals, lipids, a transferrin or a transferrin substitute, insulin or an insulin substitute, a fibroblast growth factor, less than about 0.1 mM beta-mercaptoethanol and at least one member selected from gamma-aminobutyric acid, pipecolic acid, and lithium in sufficient amounts to maintain the cells in an undifferentiated state through multiple successive culture passages and such that the cloning efficiency of the pluripotent cells is increased by at least 10% compared to pluripotent stem cells cultured in the same medium, except wherein the beta-mercaptoethanol concentration is higher than about 0.1 mM.

A related aspect of this invention is a medium including salts, vitamins, amino acids, glucose, albumin, minerals, lipids, a transferrin or a transferrin substitute, insulin or an insulin substitute, a fibroblast growth factor, less than about 0.1 mM beta-mercaptoethanol, and at least one member selected from gamma-aminobutyric acid, pipecolic acid, and lithium, in sufficient amounts to maintain stem cells grown in the medium in an undifferentiated state through multiple culture passages.

It is another object of the present invention to define culture conditions for human pluripotent stem cells that are as defined as possible, to allow the highest percentage of pluripotent stem cells in culture to continue to proliferate and be maintained in an undifferentiated state.

Other objects, features and advantages of the present invention will become apparent from the following specification.

BRIEF DESCRIPTION OF THE SEVERAL VIEWS OF THE DRAWINGS

FIGS. 3A-D show a graphical presentation of FACS data showing the high level of undifferentiated cells in the human ES cell culture grown in CM (FIGS. 3A and C) and TeSR1 medium (FIGS. 3B and D), as measured by the expression of Oct-4 (FIGS. 3A and B) and SSEA-4 (FIGS. 3C and D).

DETAILED DESCRIPTION OF THE INVENTION

Figure 1:
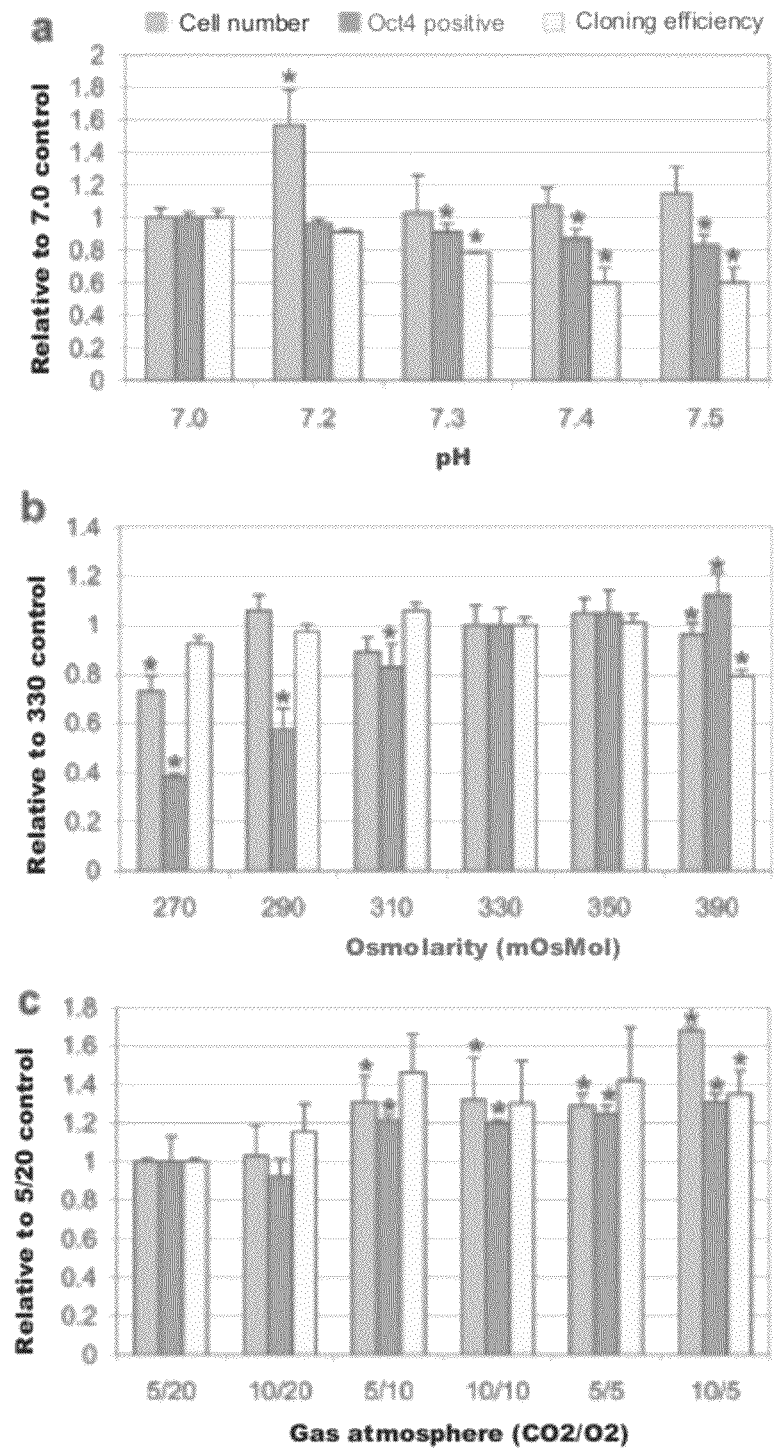
FIG. 1 illustrates optimization of physiochemical conditions for human ES cell growth; effects of altering (a) pH, (b) osmolarity, and (c) atmospheric environment on cell proliferation, cloning efficiency of the cells and spontaneous differentiation of human ES cells. For cell proliferation and spontaneous differentiation experiments, $3 \times 10^5$ cells were plated in triplicate wells and analyzed after 7 days of growth. For cloning efficiency experiments, 5000 cells were plated in triplicate wells and analyzed after 14 days of growth. For pH experiments, osmolarity was maintained at 330 mOsMol and cells were cultured in 5% $CO_2$/95% Air. For osmolarity experiments, pH was maintained at 7.2, and cells were cultured in 5% $CO_2$/95% Air. For gas atmosphere experiments, pH was maintained at 7.2, and osmolarity was maintained at 350+/−5 mOsMol. A minimum of three independent replicates (in triplicate) were performed for each parameter. Data are presented +/−SEM. *=significantly different ($P<0.05$) from standard conditions for each parameter (pH 7.0, osmolarity 330 mOsMol, atmosphere 5% $CO_2$/20% $O_2$).

Currently, large scale culturing of pluripotent stem cell lines (embryonic and induced pluripotent stem cells) for use in regenerative medicine and drug discovery applications is a major challenge in biomedical research and the pharmaceutical industry. To overcome this bottleneck, stem cell culture conditions, including medium composition, and culturing processes must become robust, reproducible, and capable of generating sufficient numbers of cells while still maintaining a stable stem cell phenotype.

To meet this challenge, the inventors describe here multiple culture conditions and media, which permit the indefinite culture and robust proliferation of primate pluripotent stem cells in an undifferentiated state with continued expression of characteristic pluripotency markers. Also, the media described are prepared in the complete absence of both feeder cells and conditioned medium.

As described here, the defined culture conditions and media are suitable for use with primate pluripotent stem cells. Pluripotent cells express one or more pluripotent cell-specific marker, such as Oct-4, SSEA-3, SSEA-4, Tra 1-60, Tra 1-81. They include, but are not limited to human ES cells (e.g., H1, H7, H9 and H14), iPS cells (e.g., iPS-Foreskin and iPS-IMR90), and vector-free iPS cells (e.g., iPS-DF19-9, iPS-DF4-3, and iPS-DF6-9), which are all available through WiCell® International Stem Cell (WISC) Bank (Madison, Wis.). iPS cells are described in Yu J. et al. *Science,* 318 (5858), pp. 1917-1920 (2007) and vector-free iPS cells are described in Yu J. et al. *Science,* 324(5928), pp. 797-801 (2009), both of these references are incorporated by reference here in their entirety. For some primate pluripotent stem cells, including iPS and vector-free iPS cells, certificate of analyses for primate pluripotent stem cells cultured on growth matrix using the fully defined medium disclosed here is available on the WISC website. Additional pluripotent stem cell lines include, but are not limited to, disease model cell lines and genetically modified lines containing marker genes.

In many embodiments of the invention, the culture conditions and media are entirely free of non-human animal products and all proteins used are of human origin. The development of these media and culture conditions make possible the derivation and maintenance of human pluripotent stem cell lines in defined and controlled conditions without direct or indirect exposure to non-human animal cells of any kind. Also, the media and culture conditions described here enable the derivation of new lines of human pluripotent stem cells which have never been exposed to non-human cells or a to medium in which animal cells were cultured. Specifically, the media disclosed here permit the culture and maintenance of primate and preferably human ES and iPS cells.

In one embodiment, the medium is free of animal products or proteins. This medium has been demonstrated to support undifferentiated pluripotent stem cell proliferation through at least twenty-five passages, which is firm evidence that it will support such cultures indefinitely. A suitable medium is capable of supporting the derivation of new human ES and iPS cell lines, and derived using the media described herein after as "new lines". These lines have passed through more than ten passages in culture.

In the past, use of conditioned medium has sometimes been referred to as creating "feeder-free" culture conditions. This phrase is a misnomer, since feeder cells of some type are still needed to condition the "conditioned medium." As described here, culture conditions permit the "feeder-independent" culture of human pluripotent stem cells. By "feeder-independent" it is meant that no feeder cells of any kind, human or animal, are needed anywhere in the process and are neither required for culture nor to condition the medium. Feeder-independent conditions do not require feeder cells at all for any purpose.

A defined and humanized medium for the culture and proliferation of human pluripotent stem cells typically includes salts, vitamins, lipids, an energy source such as glucose, minerals, amino acids, growth factors and other components. As a supplement to support cell growth, stem cell media have included serum from one source or another. Also, previously it has been reported that the addition of FGF plus a serum replacement additive permits the cultivation of human pluripotent stem cells without serum. The serum replacement additive can be a commercially available product sold for that purpose or can be a formulated mixture of proteins, including but not limited to serum albumin, vitamins, minerals, a transferrin or a transferrin substitute, and insulin or an insulin substitute. The albumin, insulin and transferrin may be recombinant proteins.

This serum replacement additive may also be supplemented with, but is not limited to, selenium and a mixture of lipids. Preferably, a defined serum replacement mix is used in lieu of serum from any source in culturing human pluripotent stem cells, to avoid variation in serum constituents and to use media that are as defined as possible. Other growth factors which have been found to be advantageous additives to the culture medium include, but are not limited to, gamma-aminobutyric acid (GABA), pipecolic acid (PA), lithium chloride (LiCl) and transforming growth factor beta (TGFβ). It has been found that TGFβ may not be needed when increasing levels of FGF are added to the medium. It is envisioned that other lithium salts can substitute for LiCl in the cell culture medium. These may include lithium salts, wherein the anion includes, but is not limited to, chloride, bromide, carbonate, citrate, sulfate, or other biologically compatible monovalent anion (see, for example, US 2004/0028656 and WO 2008/055224).

To avoid the need for a fibroblast feeder layer, previously thought to be necessary to maintain human pluripotent stem cells (ES and iPS cells) in an undifferentiated state, it is reported here that combining the use of higher concentrations of FGF (10 to 1000 ng/ml) together with the use of GABA, PA, Li and TGFβ, will enable a medium to support long term (at least three passages, and suitably 170 passages) undifferentiated stem cell growth. The combination of these additives has been found to be sufficient to maintain the culture of human pluripotent stem cells in an undifferentiated state indefinitely without exposure to either feeder cells or conditioned media. These additives are demonstrably sufficient. However, all of them may not be necessary for every medium formulation. By selective deletion of these additives, it may be empirically determined if one or more of them is not required to achieve this result for a given medium. However, it is clear that the combination is sufficient to enable a variety of media that will support the long-term culture and proliferation of undifferentiated human pluripotent stem cells without feeder cells or conditioned medium.

These additives are subject to some variation. For example, GABA is believed to interact with the GABA receptor and the scientific literature includes the identification of several molecules which are agonists of that same receptor and might be substituted for GABA in the medium as an equivalent. It is also believed that PA also interacts with the GABA receptor. While both PA and GABA were found to be helpful in the medium at the concentrations used here, it is also envisioned that one or the other of these constituents could be increased in concentration to obviate the need for the other.

The FGF in higher concentrations (40 to 100 ng/ml) seems to obviate the need for feeder cells. The preferred FGF is bFGF, also referred to as FGF2, but other FGFs, including at least FGF4, FGF9, FGF17, and FGF18, will suffice for this purpose as well. Other FGFs may also work, even if at higher concentrations, which can be empirically determined by researchers.

Figure 4:
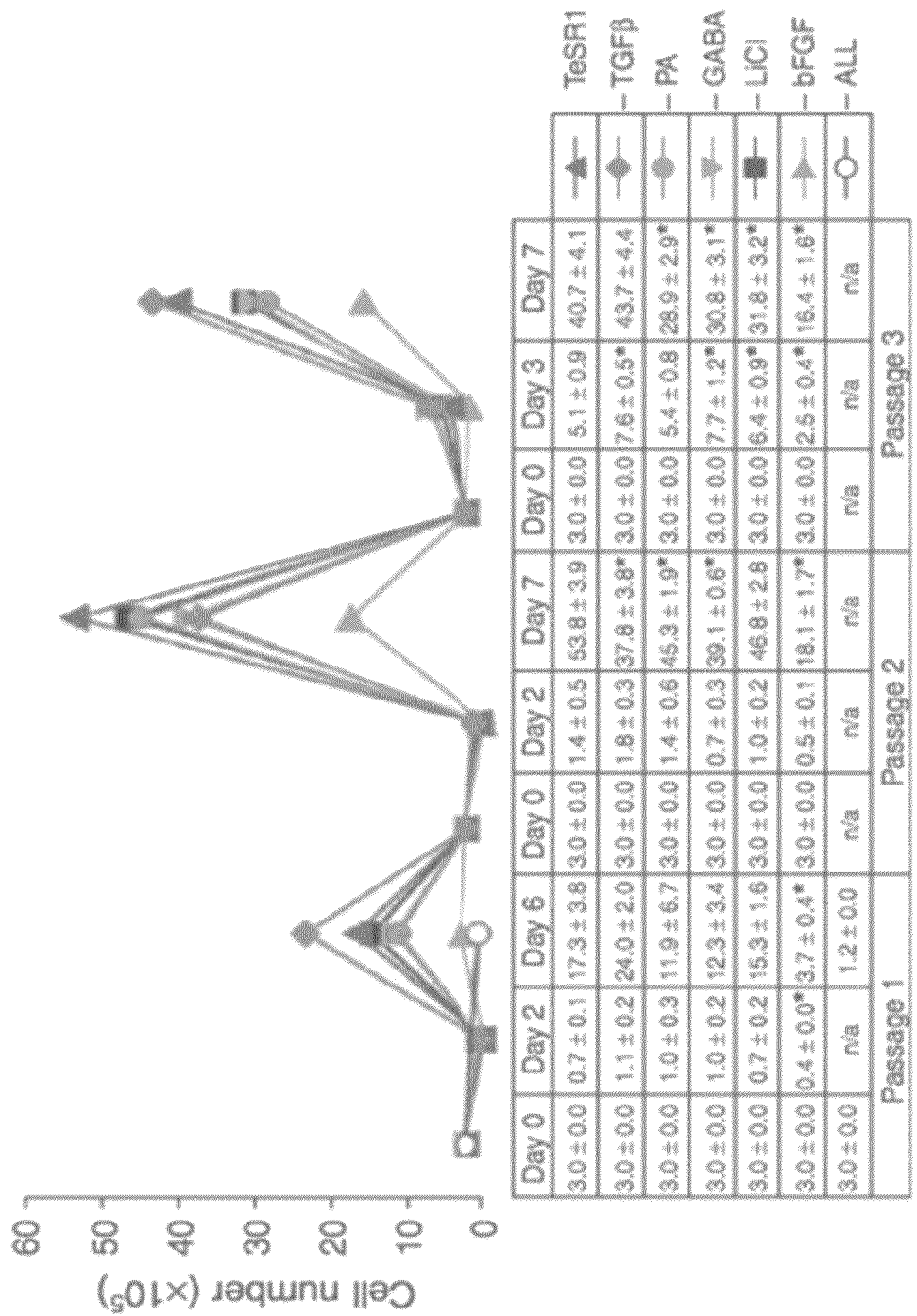
FIG. 4 is a graphical representation of data showing that the medium described here results in robust growth of pluripotent stem cells in culture. Specifically, what is shown is growth curve analysis for human ES cells cultured in complete TeSR1 (positive control), and TeSR1 minus the following individual components: TGFβ, pipecolic acid (PA), GABA, LiCl and bFGF, and TeSR1 minus all five growth factors (TeSR1—ALL or negative control); $3 \times 10^5$ cells were plated at day 0 of each passage.
Figure 5:
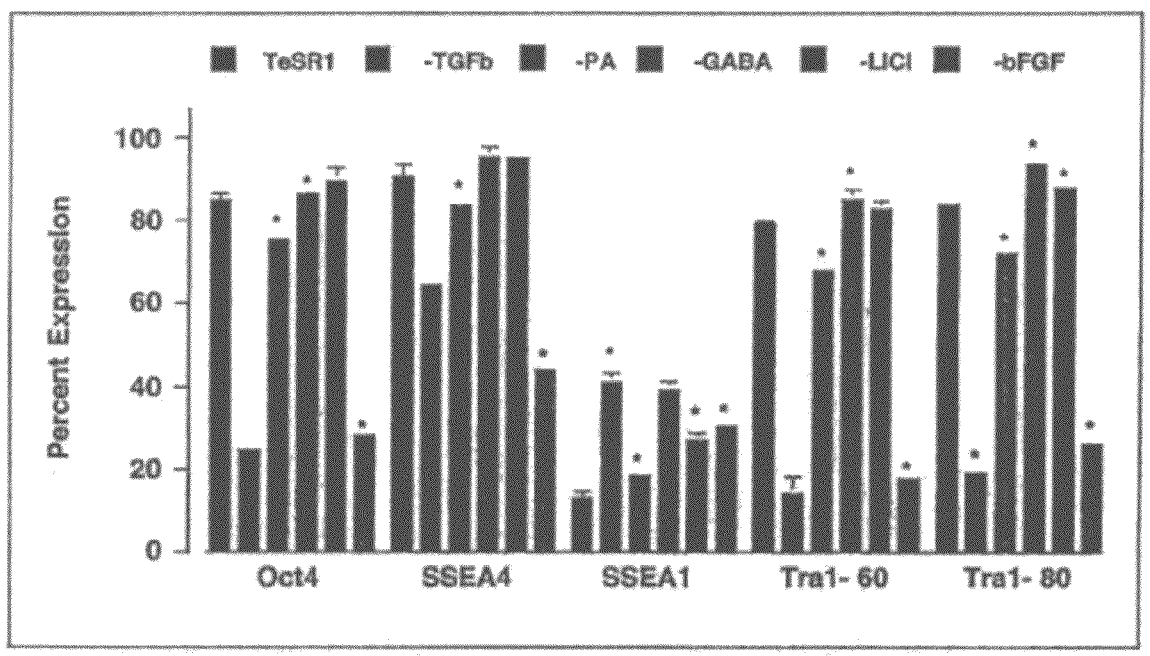
FIG. 5 shows the results of FACS analysis from experimental work described here below. This shows that the omission of each component from the medium results in an increase in the proportion of differentiated cells in the culture of human ES cells, and thus it can be inferred that the inverse is true (i.e., the addition of each component in the medium reduces the proportion of differentiated cells). This is shown through the percent expression of the human pluripotency markers Oct-4, SSEA-4, Tra 1-60 and Tra 1-81, for human ES cells cultured in complete TeSR1, and TeSR1 minus each of the following individual components: TGFβ, PA, GABA, LiCl and bFGF; data are reported +/− standard deviation; "*" indicates significant difference (t-test $P<0.05$) from TeSR1.
Figure 6:
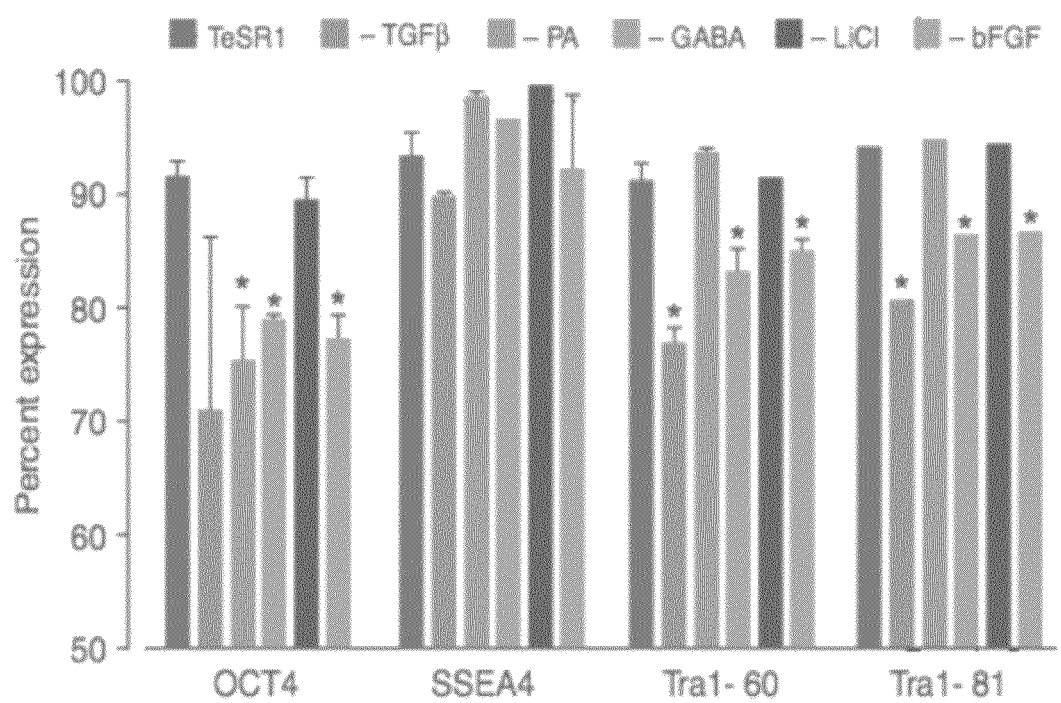
FIG. 6 shows the results of FACS analysis for human pluripotency markers Oct-4, SSEA-4, SSEA-1, Tra 1-60 and Tra 1-81 for human ES cells cultured in complete TeSR1, and TeSR1 minus each of the following individual components: TGFβ, pipecolic acid (PA), GABA, LiCl and bFGF. Triplicate wells of resulting cells were analyzed on day 6 of passage 3 by FACS for human ES cell markers. All results are presented for the H1 cell line; similar results were obtained for cell lines H7, H9 and H14. Data are reported ±standard deviation. *, significantly different (t-test, $P<0.05$) from TeSR1.

Initial subjective screens performed by the inventors identified several growth factors, chosen based on the receptors expressed by the human pluripotent stem cells, as having positive effects on undifferentiated proliferation. Of these, bFGF, LiCl, GABA, PA, and TGFβ were ultimately included in TeSR1. For each of the multiple cell lines tested, the proliferation rate and the percentage of cells maintaining expression of characteristic human pluripotent stem cell markers were higher in TeSR1 than in control cells cultured in fibroblast-conditioned medium and removal of any one of these five factors decreased culture performance. Some of these data are illustrated in FIG. 6, which shows that cultures grown in media with any one of these constituents omitted exhibited a lesser percentage of cells which remained undifferentiated as compared to cultures with all five of these medium constituents included. Note that Oct-4, SSEA-1, SSEA-4, Tra 1-60 and Tra 1-81 are all cell surface markers or transcription factors (Oct-4) which are used to track the differentiation status of stem cells. FIG. 4 illustrates similar trials in which it was demonstrated that, over multiple passages, undifferentiated cell proliferation was the highest when all these constituents together were in the culture medium.

The inventors also found it advantageous to include in the culture vessel of human pluripotent stem cells a biological matrix. One such material that has been used previously is Matrigel™, which is an artificial basement matrix of mouse cell origin, which is supplied as a commercial product free of mouse cells. However, the use of Matrigel introduces into the culture a material which is poorly defined and includes material of murine origin. Accordingly, also described here is how to create a biological matrix of human proteins that can substitute completely for the Matrigel. This matrix is composed of a blend of four human proteins: collagen isolated from human placenta, fibronectin isolated from human plasma, vitronectin isolated from human plasma or from a recombinant source, and laminin isolated from human placenta. Other extracellular matrices may be suitable for use in the present invention, which include, but are not limited to, proteoglycan, entactin, heparan sulfate, and the like, alone or in various combinations. Other suitable extracellular matrices may include, but are not limited to, Geltrex™. The major components of Geltrex™ matrix include laminin, collagen IV, entactin, and heparin sulfate proteoglycan. Also suitable are human plasma fibronectin, recombinant human plasma fibronectin, human cellular fibronectin, recombinant human cellular fibronectin, and synthetic fibronectin in combination with at least one other matrix, such as collagen. Preferred matrices of the present invention include collagen, fibronectin, vitronectin, and laminin derived matrices.

Figure 10:
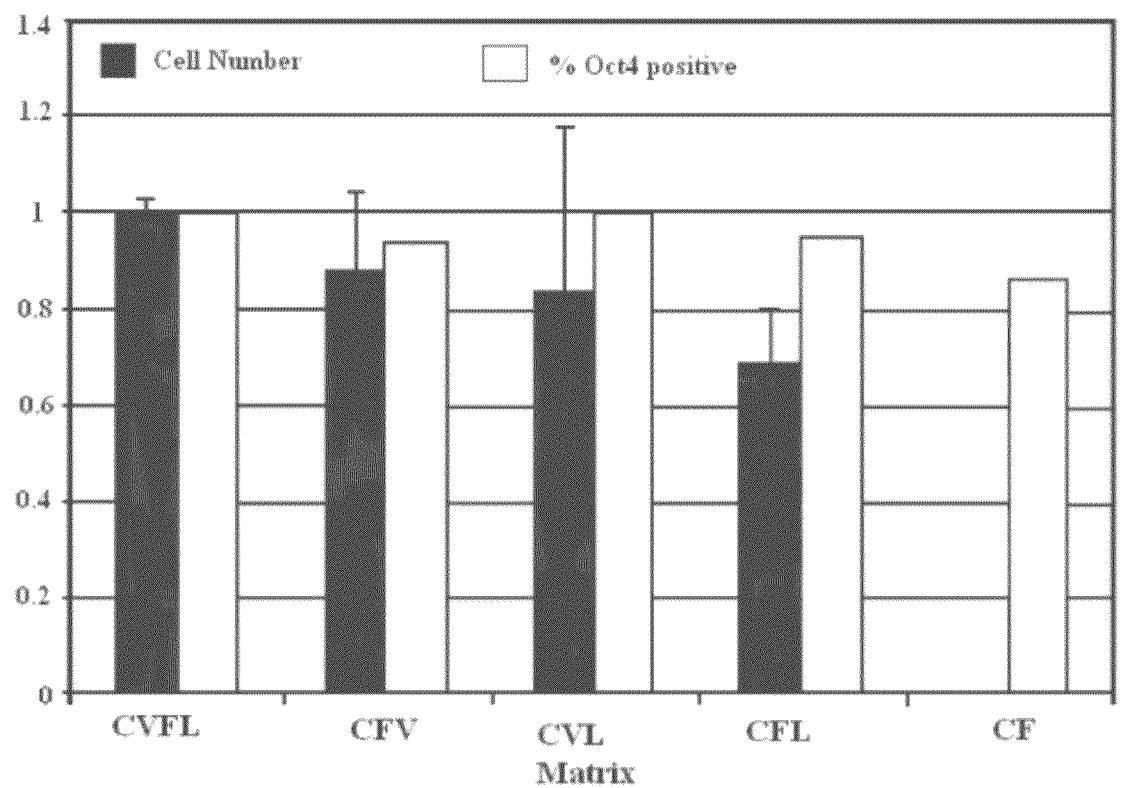
FIG. 10 shows the effect of matrix composition on cell proliferation and differentiation, as measured by Oct-4 expression and cell proliferation. CVFL refers to the Matrigel™ substitute, which contains human products or recombinant proteins, including collagen (C), vitronectin (V), fibronectin (F) and laminin (L) that support cell growth and prevent differentiation. These results show that all four matrix components are not necessary to support cell growth and prevent differentiation.

The combination of these four human proteins is sufficient, but the use of all four may not be necessary to support the growth and culture of human pluripotent stem cells, as demonstrated by the experimental results depicted in FIG. 10. For example, the use of such a matrix without one of vitronectin, fibronectin, or laminin, but including the other three matrix proteins, does support the culture of pluripotent stem cells, with some loss of purity in the state of differentiation of the ES or iPS cell culture. Likewise, it is envisioned that the use of such a matrix without two of vitronectin, fibronectin or laminin, does support the culture of pluripotent stem cells, with some loss of purity in the state of differentiation of the ES or iPS cell culture. Suitable matrix protein combinations include collagen and fibronectin, collagen and vitronectin, and collagen and laminin. The method of making the matrix for pluripotent stem cell growth is described in the examples below.

To arrive at the above-listed medium additives, the inventors methodically tested over 80 individual media components, including growth factors. While some of the additives seemed, at least for a few passages, to support the growth of human pluripotent stem cells in culture, many failed in subsequent passages to maintain the pluripotent stem cells in an undifferentiated state. The inventors were able to identify combinations of specific growth factors useful in the medium described in the examples below.

Also, through methodical testing, the inventors were able to investigate the effects of varying the concentration of β-mercaptoethanol (BME) in the TeSR1 medium, when culturing primate pluripotent stem cells. It was found that BME is one of various parameters in a culture medium that affects cloning efficiency of pluripotent cells in a positive manner. Specifically, when BME was either omitted or used in a concentration less than about 0.1 mM (between about 0 to about 0.1 mM) in the TeSR1 medium, the cells continued to proliferate (see FIG. 15a-b) with minimal to no change in the differentiation status of the cells (see FIG. 15c). Most notably, however, the cloning efficiency of the cells increased by at least 10% and preferably 20%, 30%, 40%, 50%, 60%, 70%, 80%, 90%, and 100% (see FIG. 15a) in comparison with pluripotent cells cultured in the same medium having higher than about 0.1 mM BME.

Accordingly, in one embodiment of the invention, a medium is disclosed for increasing the cloning efficiency of pluripotent cells in culture, wherein the medium contains salts, vitamins, amino acids, glucose, a fibroblast growth factor, less than about 0.1 mM beta-mercaptoethanol, and at least one member selected from gamma-aminobutyric acid, pipecolic acid, and lithium, in sufficient amounts to maintain stem cells grown in the medium in an undifferentiated state through multiple culture passages, wherein the cloning efficiency of the cells increases by at least 10% compared to the medium containing greater than or equal to 0.1 mM BME.

In another embodiment, a method is disclosed for increasing cloning efficiency of cells in culture by at least 10% through culturing the primate pluripotent stem cells on a matrix in a medium without feeder cells or conditioned media, the medium comprising salts, vitamins, amino acids, glucose, a fibroblast growth factor, less than about 0.1 mM beta-mercaptoethanol and at least one member selected from gamma-aminobutyric acid, pipecolic acid, and lithium in sufficient amounts to maintain the cells in an undifferentiated state through multiple successive culture passages. In a related embodiment, when gamma-aminobutyric acid, pipecolic acid, lithium, and transforming growth factor beta are added in sufficient amounts to maintain the human stem cells in an undifferentiated state, at least 90% of the cells in culture are positive for the transcription factor Oct-4 through multiple successive culture passages.

In general, the observation that human pluripotent stem cell cultures have previously been maintained in an undifferentiated state only when cultured in the presence of fibroblast feeder cells or in a conditioned medium has led to speculation that the fibroblasts release a factor into the medium, which acts to inhibit human pluripotent stem cell differentiation. The data presented here demonstrate that this not the case. However, whatever effect fibroblast feeder cells have on culture medium, it is now clear that the media described below will substitute for that effect. The media described below, as defined, contain no non-human cells, and permit the long-term culture of undifferentiated human pluripotent stem cells. This strategy enables the preparation of a "humanized" medium and matrix to avoid any possible concerns about sub-cellular products of non-human origin.

Table 1 describes a defined medium developed by the inventors. All of the medium components and their preferred concentrations are listed in the table. It is envisioned that concentration ranges that are at least 10× higher or 10× lower than the concentrations listed in Table 1 may be able to support culture and derivation of primate pluripotent stem cells. The complete medium is designated TeSR1. The TeSR1 medium is comprised of a DMEM/DF12 base, supplemented with human serum albumin, vitamins, antioxidants, trace minerals, specific lipids and cloned growth factors.

Based on the formulation of TeSR1 in Table 1, it is expected that a suitable concentration range for a salt in the medium is from about 0.1 mM to about 100 mM. A suitable range for a vitamin is from about 1.0 E-05 mM to about 2.5 mM. A suitable range for an amino acid is from about 1.0 E-03 mM to about 30 mM. A suitable range for a mineral is from about 1.0 E-07 mM to about 10.0 E-02 mM. A suitable range for a lipid is from about 8.0 E-06 mM to about 1.0 E-02 mM. A suitable range for glucose is from about 1.0 mM to about 150 mM. A suitable range for a fibroblast growth factor is from about 0.1 ng/ml to about 1000 ng/ml. A suitable range for gamma-aminobutyric acid is from about 0.1 mM to about 10 mM. A suitable range for pipecolic acid is from about 1.0 E-04 mM to about 1.0 E-02 mM. A suitable range for lithium is from about 0.1 mM to about 10 mM. A suitable range for a transforming growth factor beta is from about 1.0 E-09 mM to about 2.0 E-07 mM. A suitable range for insulin is from about 4.0 E-04 mM to about 4.0 E-02 mM. A suitable range for transferrin is from about 1.0 E-05 mM to about 1.0 E-03 mM. Also, a suitable concentration range for albumin is from about 2.0 E-02 mM to about 2.0 mM.

Because human serum albumin (HSA) is expensive, the inventors routinely use bovine serum albumin (BSA) as a less costly substitute. Although the species source of the albumin is different, BSA in the TeSR medium (mTeSR1) functions the same as its humanized counterpart, TeSR1 medium, which contains HSA. This humanized version of TeSR has been renamed and is currently marketed as TeSR2 by Stem Cell Technologies (Vancouver, BC, Canada).

Figure 12:
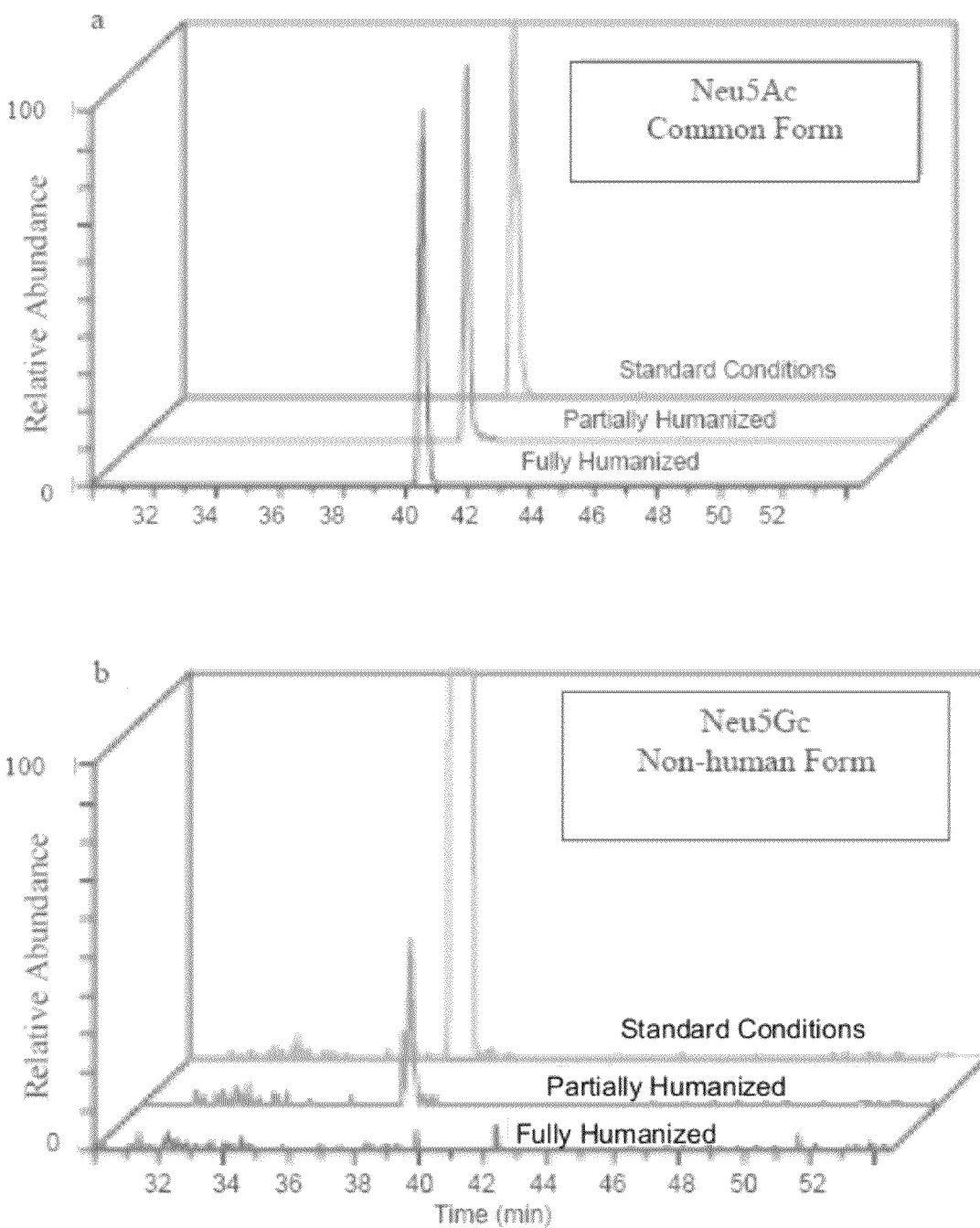
FIG. 12 illustrates the absence of sialic acid contamination in human ES cells cultured in defined conditions. Human ES cells grown under different conditions were analyzed by LC-MS for the sialic acids Neu5Ac and Neu5Gc: (a) the common form, NeuAc was found abundantly expressed on cells regardless of culture conditions with peak intensities in the range of $1-3\times 10^8$ (traces autoscaled); and (b) the non-human Neu5Gc was found on human ES cells grown under standard (conditioned medium) conditions (peak intensity off scale at $5 \times 10^5$), it was reduced but detectable in partially humanized conditions with peak intensity of $4 \times 10^4$, and no detectable Neu5Gc was found on cells grown in fully humanized conditions. Growth conditions key: Standard Conditions=mouse embryonic fibroblast conditioned media on Matrigel (orange). Partially Humanized=TeSR1 medium on Matrigel (green), Fully Humanized=TeSR1 medium on human matrix components (blue).

Also described below is the derivation of new lines of human pluripotent stem cells using TeSR1 (see Ludwig T. E. et al. *Nat. Biotech.* 24(2), 185-187 (2006) and related Supplementary results, incorporated by reference here in its entirety). The human pluripotent stem cell lines, such as ES and iPS cells, disclosed herein and provided in the corresponding Ludwig (2006) paper have never been exposed to feeder cells, conditioned medium, non-human animal products or non-human animal proteins. It has previously been reported that prior human ES lines exhibit a sialic acid form (Neu5Gc) that is not natively found in human cells whether in culture or in the body. Since the prior human ES lines acquired the Neu5Gc from culture conditions including murine components, the new human ES cell lines described here are and will be entirely free of Neu5Gc (FIG. 12).

The invention will be more fully understood upon consideration of the following non-limiting Examples. In the Examples, pluripotent stem cells, including human ES cells and iPS cells, were cultured in TeSR1 medium (set forth in Table 1 below) and variations of the medium where certain components have been removed. It is specifically contemplated that the methods disclosed are suited for primate pluripotent cells generally as pluripotent cells, regardless of their origin, operate in substantially the same manner in the disclosed methods. Accordingly, the media and methods disclosed here are suitable for culturing primate iPS cells.

EXAMPLES

Inventors used human ES cell lines H1, H7, H9 and H14 (Thomson, J. A. et al. *Science* 282, 1145-1147 (1998)) in a program of human ES cell media optimization that included modifications to the physiochemical environment, growth factor supplements and matrix components. To accomplish this, human ES cell lines H1, H7, H9, and H14 were cultured on Matrigel (Becton Dickinson) in fibroblast-conditioned medium as previously described (Xu, C. et al. *Nature Biotechnology* 19, 971-974 (2001)). Cells were transitioned into test media by direct passage from conditioned medium. Cultures of human ES cells were routinely passaged in clumps at approximately weekly intervals onto Matrigel or human matrix-coated plates by exposure to dispase (2.0 or 0.5 mg/ml respectively: Invitrogen). Following 7 minutes of dispase exposure, cells were rinsed 3 (three) times on the plate with medium, followed by gentle scraping to collect. Colonies were further broken up by gentle pipetting and then plated. The human matrix-coated plates were composed of 10 μg/cm² human collagen IV (Sigma or Becton Dickinson), 0.2 μg/cm² human vitronectin (Sigma), 5 μg/cm² human fibronectin (Sigma or Becton Dickinson) and 5 μg/cm² human laminin (Sigma). During the course of these studies we successfully used 4 lots of fibronectin, 2 lots of collagen, 3 lots of laminin, and 3 lots of vitronectin. For growth curve proliferation studies, 3-5×10⁵ cells were plated on Day 0 of each passage into conditioned medium, TeSR1 or TeSR1 minus the following components: TGFβ, PA, GABA, LiCl and bFGF. Cells were cultured for three passages. Cells were harvested on Day 2-3 and Day 6-7 and counted using a Trypan Blue exclusion assay. At the end of passage three, cells were individualized by treatment with trypsin/EDTA and were analyzed by FACS for human ES cell markers Oct-4, SSEA-4, Tra 1-60 and Tra 1-81 as subsequently described.

Specifically, to optimize the physiochemical environment, human ES cells with an EGFP reporter gene and a neomycin resistance cassette under control of the endogenous Oct-4 gene were utilized for the physiochemical optimization assays. Cells were treated with G418 (Invitrogen) for at least 4 days prior to the start of the assay to ensure a pure stem cell population upon initiation. At the end of the growth period, cells from independent wells were individualized by treatment with trypsin/EDTA, counted and subjected to FACS analysis as subsequently described. To determine cloning efficiency of the cells, resulting colonies were stained with BCIP/NTB alkaline phosphatase substrate kit IV (Vector Laboratories) and counted. Percentages were determined by dividing colony number obtained by the initial number of cells plated. Our analysis of physiochemical culture conditions suggested that undifferentiated human ES cell proliferation was optimal at a pH of 7.2, an osmolarity of 350 mOsMol and an atmosphere of 10% $CO_2$/5% $O_2$ (FIG. 1). These conditions were used for all subsequent cultures described herein.

Figure 2:
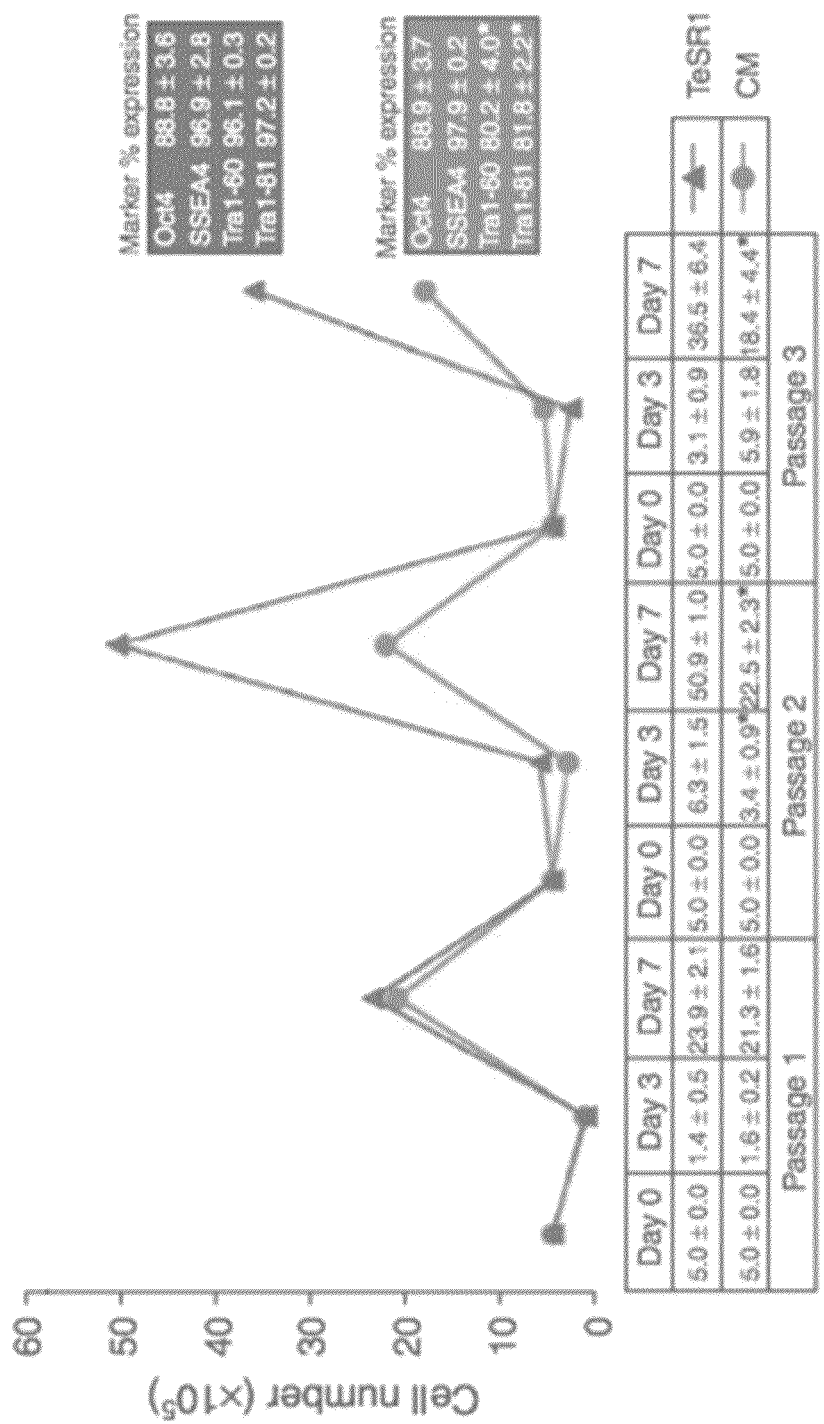
FIG. 2 shows growth curves for human ES cells cultured in TeSR1 versus conditioned medium (CM) that are plotted over three passages starting with an equivalent number of cells at day 0 for each passage ($5 \times 10^5$ cells); for each passage, cell counts are reported ($1 \times 10^5$ cells) from triplicate wells at day 3 and day 7; at the end of the third passage, cells from triplicate wells were collected an analyzed by FACS for human ES cell-specific markers. In eight replicates of this experiment using four different human ES cell lines, the number of cells at the end of three passages was always greater in TeSR1 than in conditioned medium. In the same replicates, the percentage of cells expressing ES cell markers in TeSR1 was either higher than or equivalent to the percentage in conditioned medium. CM, conditioned medium.
Figure 3A:
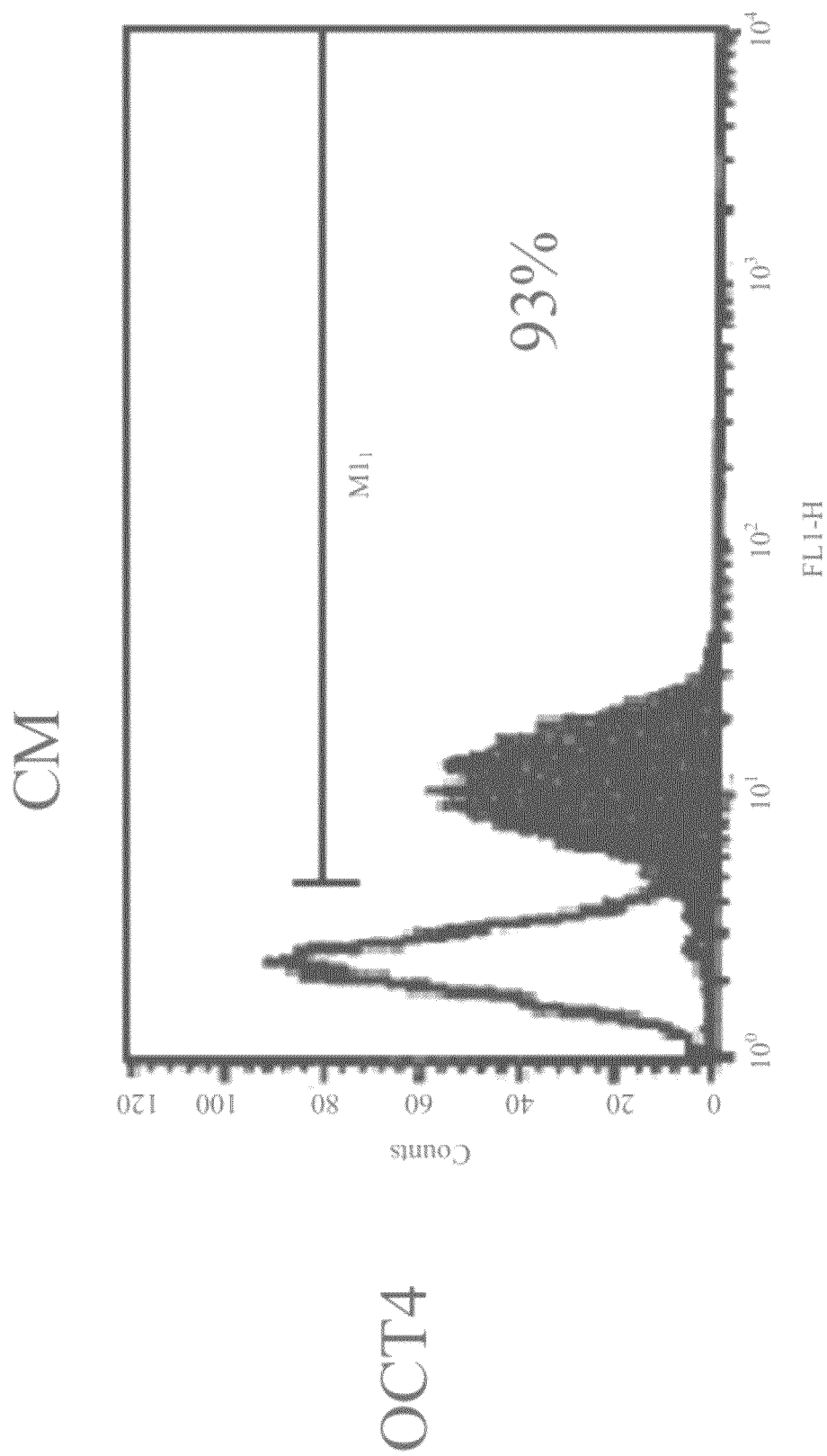
Figure 3B:
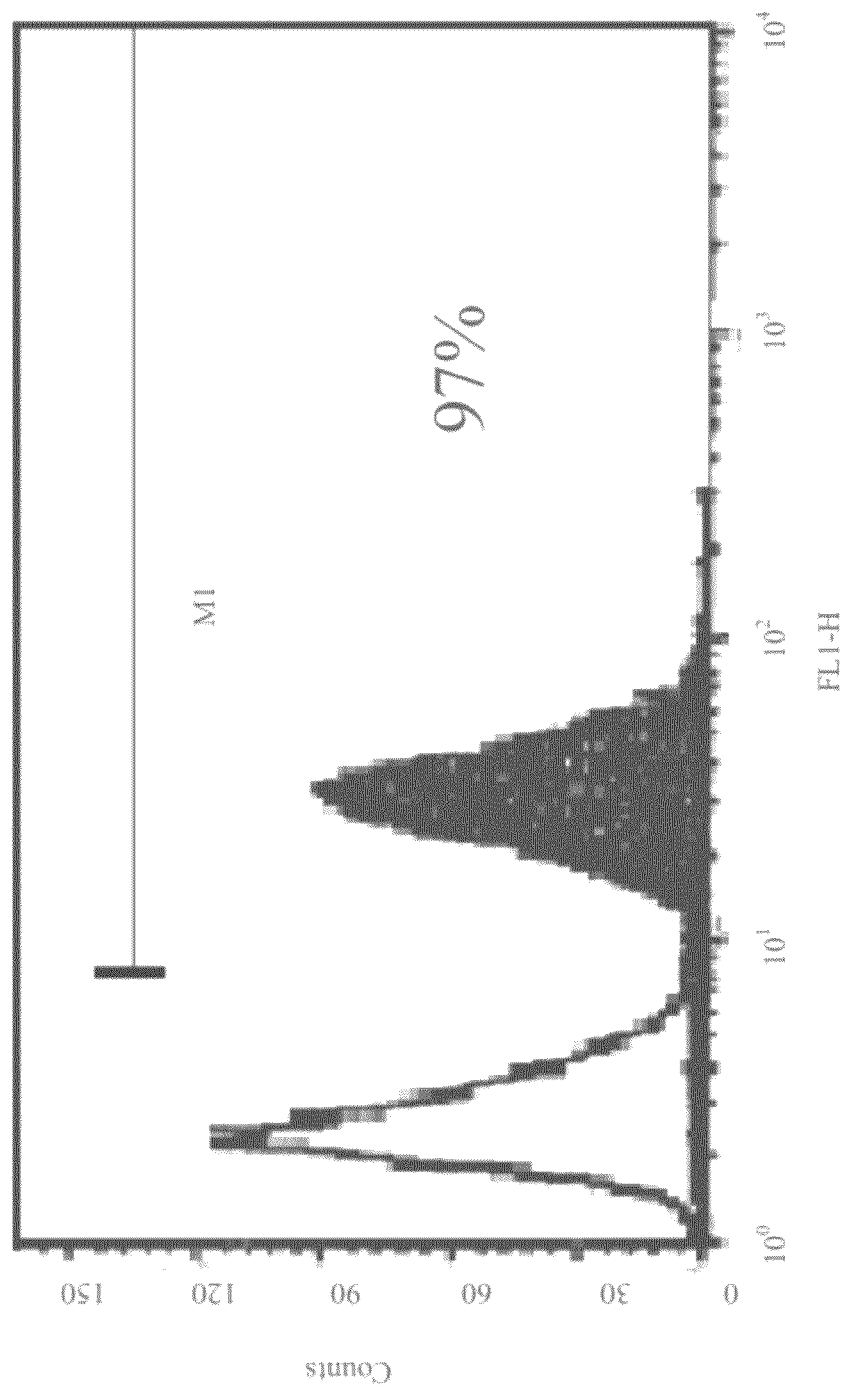
Figure 3D:
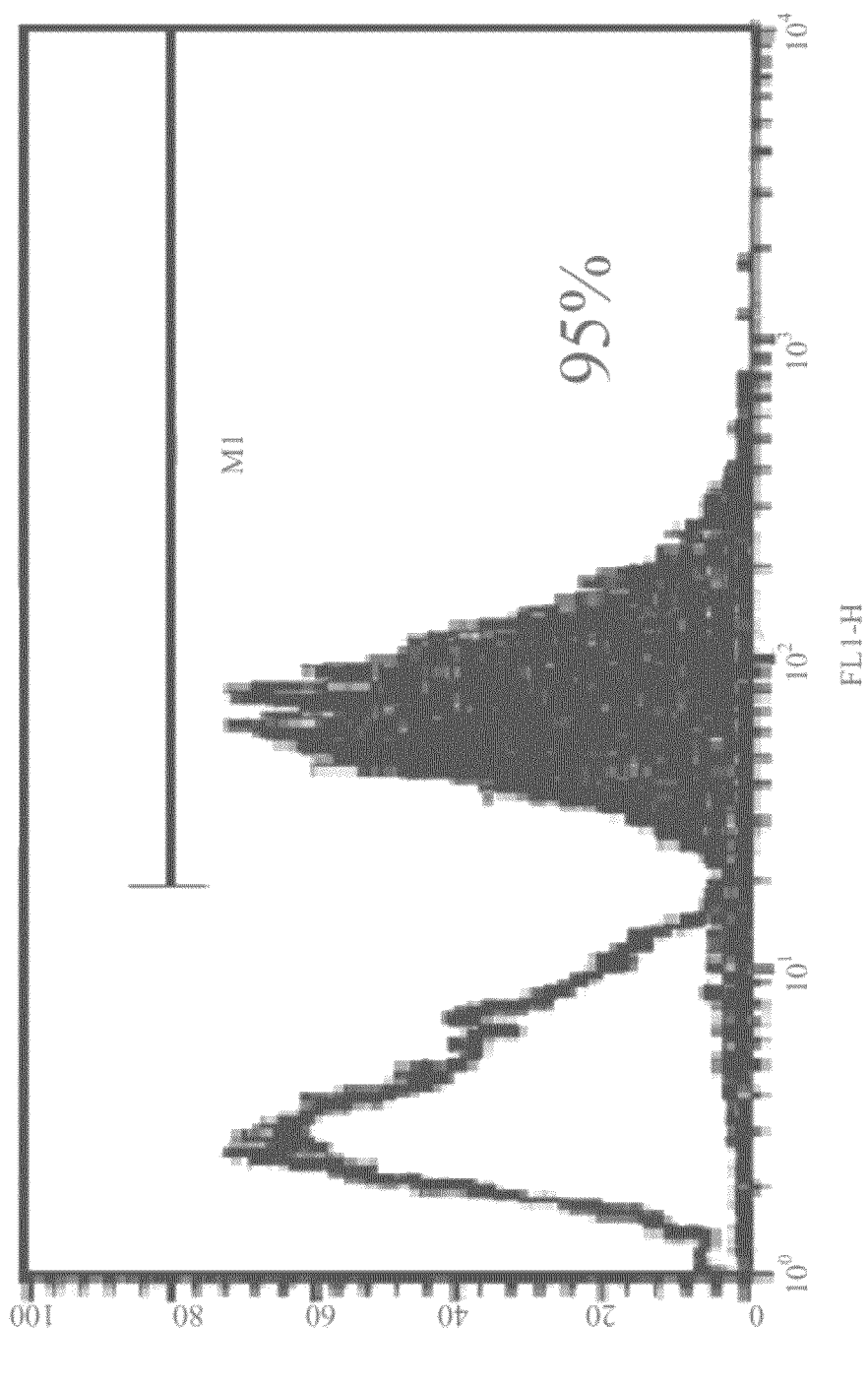

An initial subjective list of growth factors was selected for testing based on receptors expressed by human ES cells. (See Sperger, J. M. et al. *Proc. Natl. Acad. Sci. USA* 100, 13350-13355 (2003)). Several were found to have a positive effect on undifferentiated proliferation. Of these, bFGF, LiCl, GABA, PA and TGFβ were ultimately included in TeSR1. To test the conditions of the ES cell colonies and the suitability of the culture for the long-term maintenance of human ES cell cultures, the TeSR1 medium was compared to the best prior medium condition, which, in the inventor's hands, is the use of conditioned medium. It was found that the TeSR1 medium was capable of increasing cellular proliferation (FIG. 2) and maintaining the human ES cells in such an undifferentiated state that over 90% of the cells continued to test positive for Oct-4 even after long-term culture (FIG. 3). This represents the first known instance in which any medium, free of both feeder cells and conditioned medium, has maintained undifferentiated growth of human pluripotent stem cells such that over 90% of the cells in the culture remain undifferentiated.

Using the media and culture system described here, it is now possible to establish and maintain primate pluripotent stem cell lines that comprise at least 70%, at least 80%, more preferably at least 85 to 89%, more preferably at least 90%, and most preferably at least 91 to 99% undifferentiated stem cells.

Several factors were found to have a positive effect on undifferentiated proliferation. Of these, bFGF, LiCl, GABA, PA, and TGFβ were ultimately included in TeSR1. Removal of any one of the five factors significantly decreased some parameter of culture performance, but only the removal of bFGF consistently decreased both the total cell number and the percentage of cells expressing ES cell markers (FIGS. 2, 4 and 6). When exogenous bFGF was removed, some undifferentiated cells nonetheless persisted through at least three passages (FIGS. 2, 4 and 6). If all five factors were removed, however, culture was not sustainable beyond the first passage (FIGS. 2, 4 and 6).

While a medium with all of the above constituents is sufficient and is preferred, not all of the components are necessary for the successful culture of human pluripotent stem cells. Depending on the amount of differentiated cells one is willing to tolerate, some of the components of the medium can be omitted, particularly if the medium is only used for a few passages. To further explore which constituents might be omitted, human pluripotent stem cells were cultured on variants of the above medium with differing components omitted. Two hundred thousand cells were plated and grown for seven days on each experimental medium, two wells per treatment. The cells were then assayed for expression of the transcription factor Oct-4, a recognized marker of undifferentiated cells.

Figure 7:
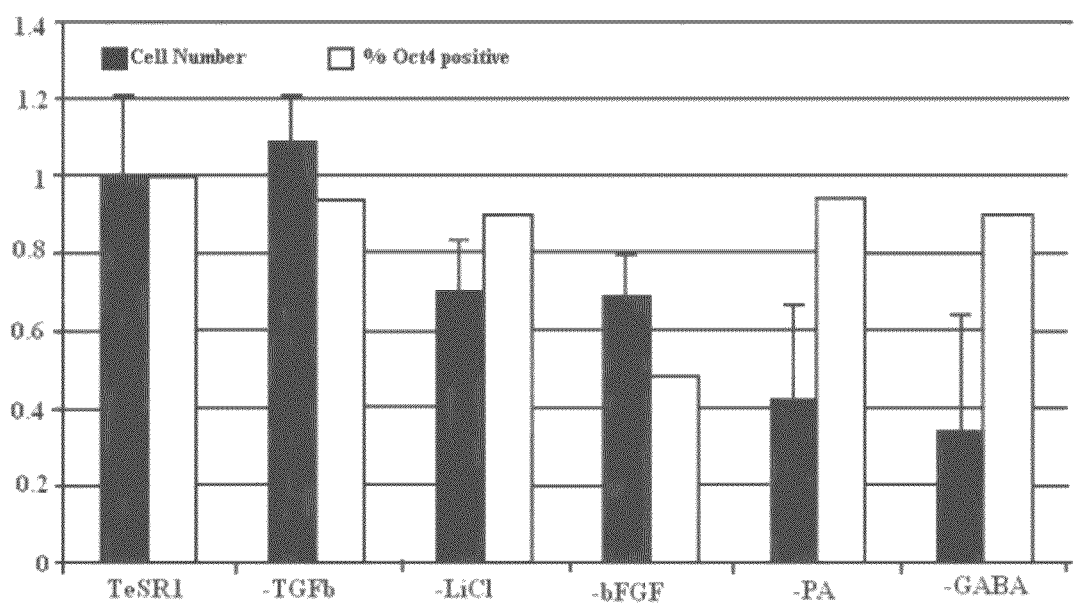
FIG. 7 shows the results of FACS analysis for human pluripotency markers Oct-4, and cell proliferation of human ES cells cultured in complete TeSR1, and TeSR1 minus each of the following individual components: TGFβ, LiCl, bFGF, pipecolic acid (PA) and GABA.

The data from that experiment are presented graphically in FIG. 7, where the numbers of Oct-4 expressing cells in each experimental medium are presented as a fraction of that from the preferred medium TeSR1. Note that TGFβ seems to be the least necessary component, at least in the presence of high levels of FGF for short-term culture. Also, note that omitting other constituents (e.g., LiCl, bFGF, PA, or GABA) does result in increased percentages of undifferentiated cells in the culture. The difference between the percentage of undifferentiated cells and the omitted constituent is quantitative. Regardless of the omitted constituent, the medium does work, at least to some degree for limited cell passages, without each of the omitted components.

Figure 8A:
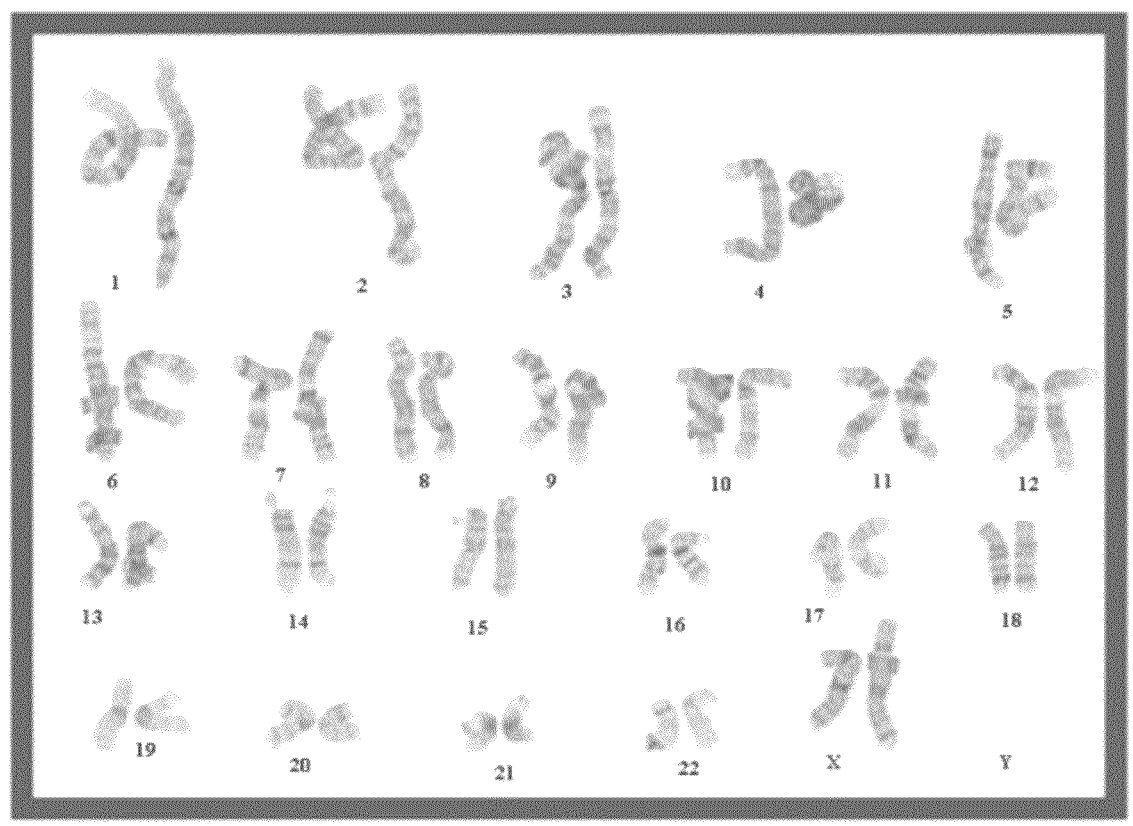
FIGS. 8A-B show the karyotype analysis of human ES cells cultured in TeSR1 medium; H9 (a) and H14 (b) cell lines were maintained in TeSR1 medium on Matrigel matrix for 21 and 7 passages (FIG. 8A), respectively, and subjected to cytogenetic analysis using G-banding (FIG. 8B); 20 metaphase cells from each cell line were evaluated. A normal karyotype was observed for all cells examined.
Figure 8B:
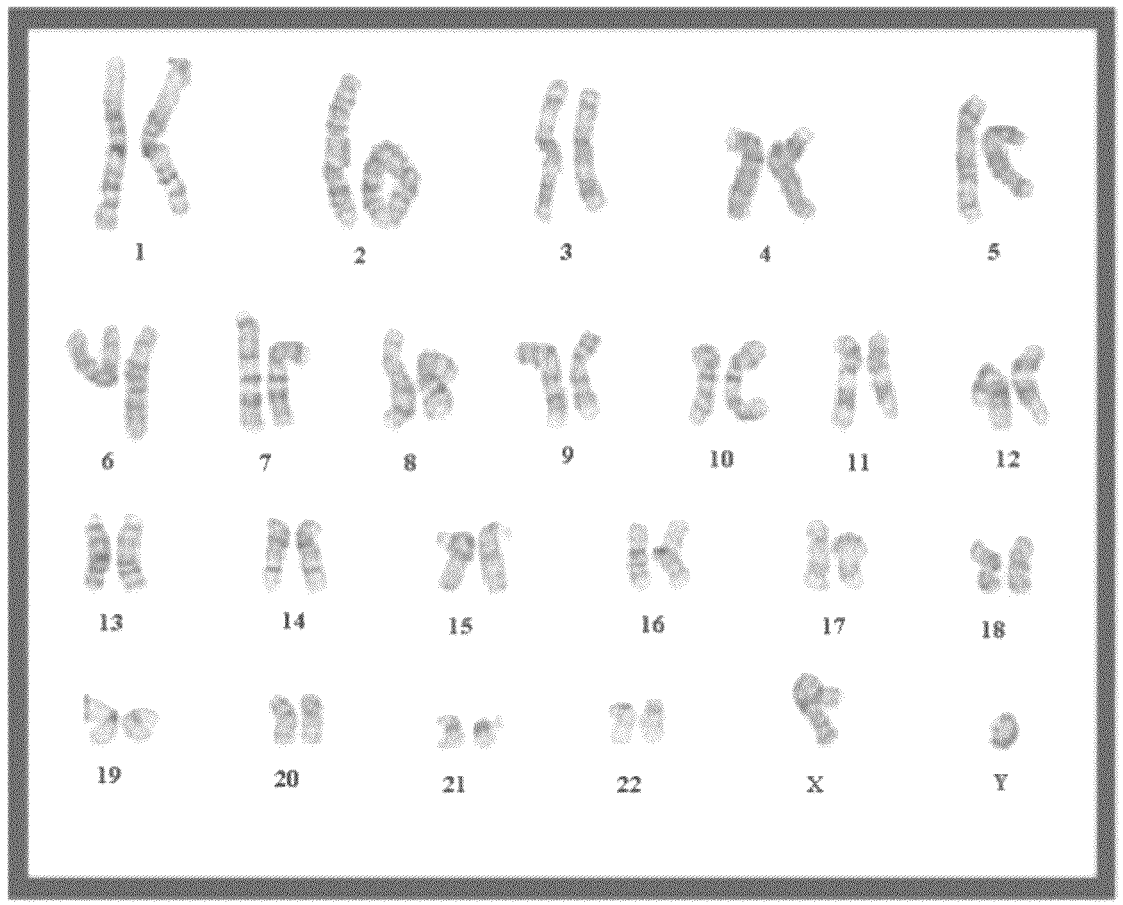
Figure 9:
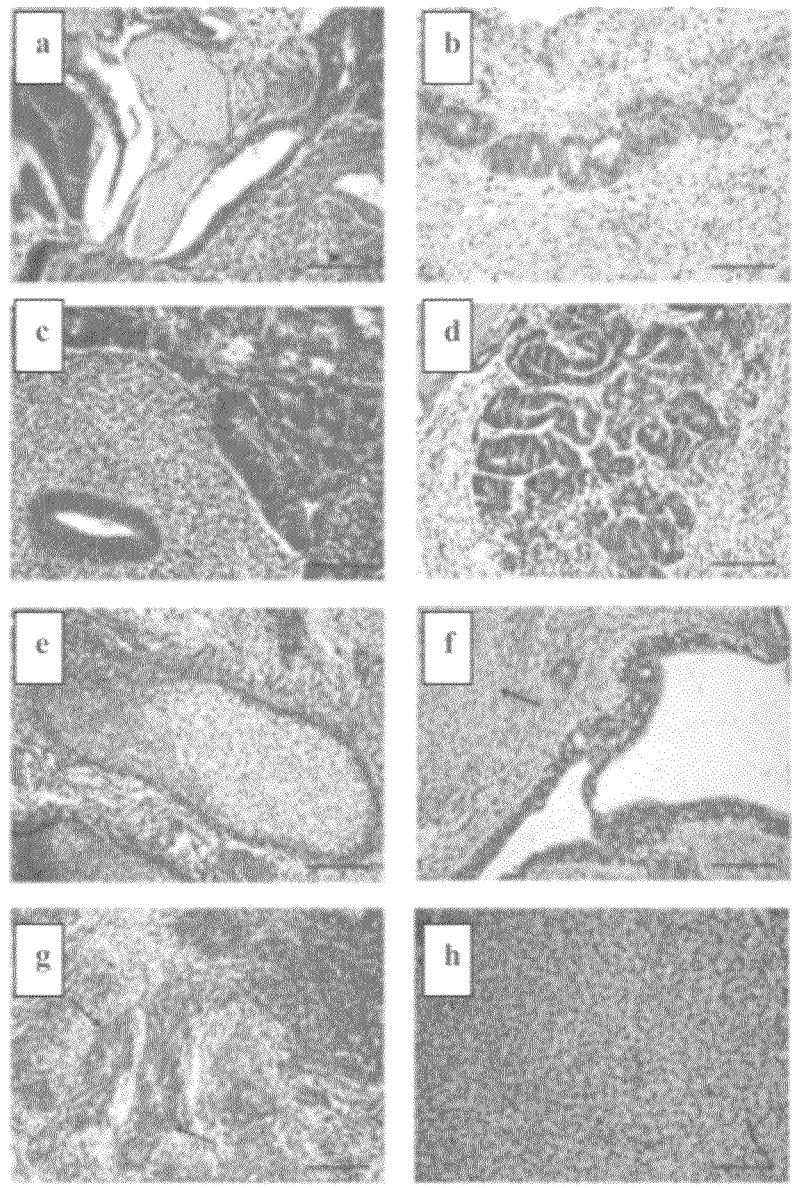
FIG. 9 illustrates pluripotency of human ES cells maintained in TeSR1 medium; H1 and H9 cells were cultured in TeSR1 medium on Matrigel for 11 and 20 passages, respectively, and injected into the rear leg muscle of 4-week-old SCID-beige mice. Teratomas exhibiting complex differentiation developed in the mice 6-8 weeks post-inoculation: (a) bone, H9 cell line, (b) epithelial acinar structure, H1 cell line, (c) epithelial luminal structure, H9 cell line, (d) epithelial luminal structure, H1 cell line, (e) cartilage, H9 cell line, (f) cartilage with epithelial structure, H1 cell line, (g) rosettes of neural epithelium, H9 cell line, (h) and loosely structured mesenchyme, H1 cell line; scale bar=100 um.

Cells of human ES cell lines H1, H7, H9 and H14 cells have all proliferated robustly in TeSR1 for 11, 7, 25, and 17 passages respectively (2-6 months). The karyotypes were confirmed normal for cell line H14 after 7 passages and H9 after 8 and 21 passages (FIG. 8). Teratoma formation was confirmed for H1 and H9 after 11 and 20 passages, respectively (FIG. 9).

Initial experiments with TeSR1 medium were all performed on Matrigel, a basement membrane preparation extracted from a murine Englebreth-Holm-Swarm sarcoma. Matrigel effectively supports long-term proliferation of human pluripotent stem cells in TeSR1 medium, but it is a complex mixture of murine proteins and is a significant source of variability in culture. After screening a variety of components individually and in combination, the inventors developed a new matrix material of human origin composed of the following four proteins:

1. Collagen (isolated from human placenta) at a final concentration of 10 μg/100 μl/cm².
2. Fibronectin (isolated from human plasma) at a final concentration of 5 μg/100 μl/cm².
3. Vitronectin (isolated from human plasma) at a final concentration of 0.2 μg/100 μl/cm².
4. Laminin (isolated from human placenta) at a final concentration of 5 μg/100 μl/cm².

To assemble this matrix, the collagen is denatured with 6M GuHCl (guanidine HCl), filtered through a 0.45 micron filter and frozen in aliquots. Upon thaw, denatured collagen was diluted into Ca- and Mg-free phosphate buffered saline (PBS), to achieve the appropriate final concentration and was then plated. The coated plates were allowed to incubate at room temperature for no less than 1 hour before the additional matrix components were plated. Following this initial incubation, additional matrix components (fibronectin, vitronectin and laminin) were diluted into a Ca- and Mg-free PBS to achieve the appropriate final concentration and plated. The coated plates were allowed to incubate at room temperature for no less than 1 hour before human pluripotent stem cells, such as ES and iPS cells) were plated.

Figure 11:
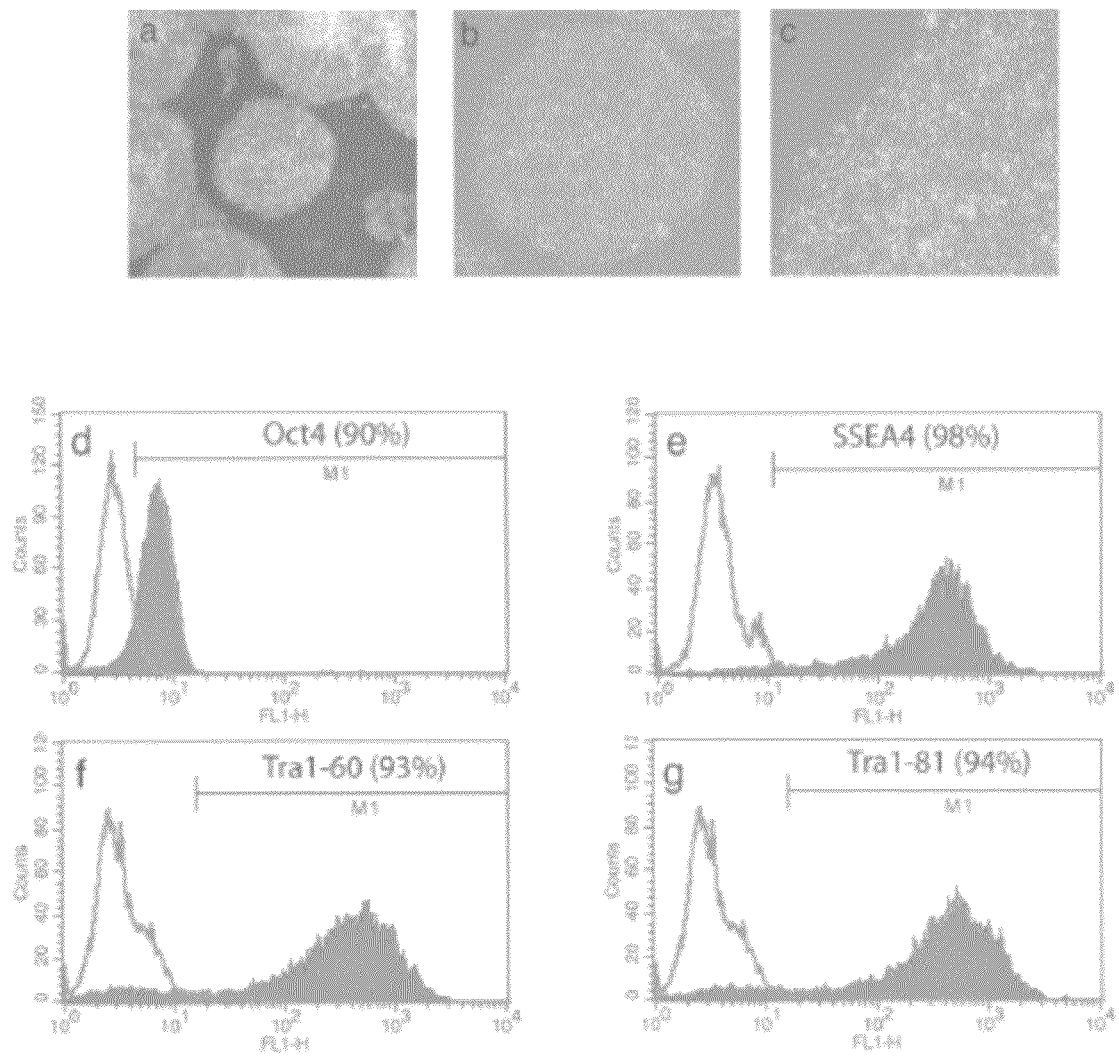
FIG. 11 shows representative morphology and FACS analysis of human ES cells cultured in defined, feeder-independent conditions. Human ES cells were cultured for 5 passages in TeSR1 on human matrix and then photographed at magnifications of 2× (a), 4× (b), and 10× (c) using phase contrast microscopy. Cells were analyzed for internal (Oct-4) or cell surface (SSEA-4, Tra 1-60, Tra 1-81) markers after 11 passages of culture in TeSR1 on human matrix components (d-g). The level of undifferentiation is identified as 90% or greater based on percent positive cell marker expression listed in parentheses and data presented are from the H1 cell line. Similar results were obtained using the H9 cell line with 16 passages of culture in TeSR1 on human matrix components.

The combination of four human proteins was found to support robust, long-term proliferation of human pluripotent stem cells in TeSR1. Using the new matrix material, human pluripotent stem cells of previously existing lines have been cultured for a minimum of 10 passages while remaining undifferentiated and proliferating. Specifically, cell lines H1 and H9, cultured in TeSR1 on the human matrix for 11 and 16 passages, respectively, continued to express markers characteristic of human ES cells (FIG. 11). Human ES cells cultured for 5 passages in TeSR1 on human matrix continued to show morphology characteristics of ES cells, and to express markers characteristic of ES cells (FIG. 11). Analyses for internal (Oct-4) or cell surface (SSEA4, Tra 1-60, Tra 1-81) markers after 11 passages of culture in TeSR1 on human matrix components (FIG. 11d-g) were all greater than 90% percent positive.

To test the strict necessity for the components of the humanized matrix, variations on the matrix were formulated with one or more components omitted. The data from that experiment is presented in FIG. 10. Note that CFV, CVL and CFL matrices do work well and maintain human pluripotent stem cells, such as ES and iPS cells, in an undifferentiated state. Also, as described above, it is envisioned that CV, CF, and CL could also maintain cell growth and prevent differentiation. Morphological assessment and visual observations of attachment suggest that using only two components of the humanized matrix one can achieve attachment, although at a lower rate than with three or four components. The CVFL matrix is simply more conducive to cell culture growth. Generally, CVFL matrices provide greater attachment than CFV, CVL, or CFL matrices, which in turn provide greater attachment than CF, CL, or CV matrices (these observations represent three replicates; data not shown).

Figure 15:
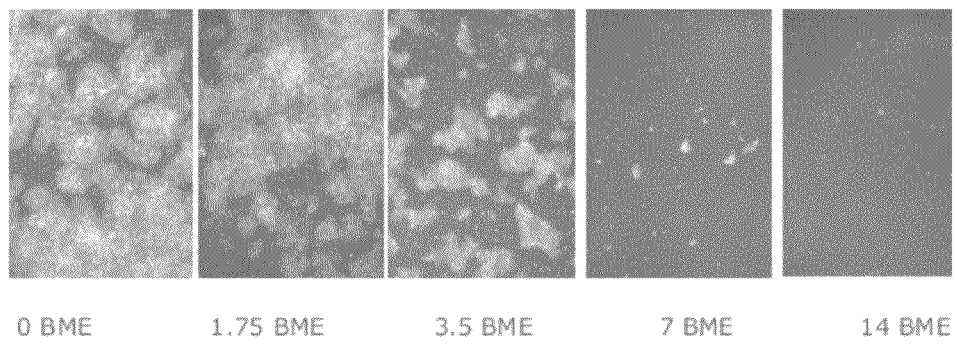
FIG. 15 illustrates the growth of hES cells grown in mTeSR1 with five different concentrations of beta mercaptoethanol (βME). ES03-DL1-K were grown for one to five passages, visualized (a), counted to determine proliferation and cloning efficiency (b), and stained using Trypan Blue for Oct-4 and SSEA-4 to identify differentiation status of the cells (c). The treatment concentrations consisted of 0, 1.75, 3.5, 7, and 14 µL βME/500 mL of total TeSR1 media. Results shown are the mean from growth in 3 wells/treatment. This experiment was repeated multiple times both with ES03-DL1-K and H9-WA09 cells with similar results.
Figure 15:
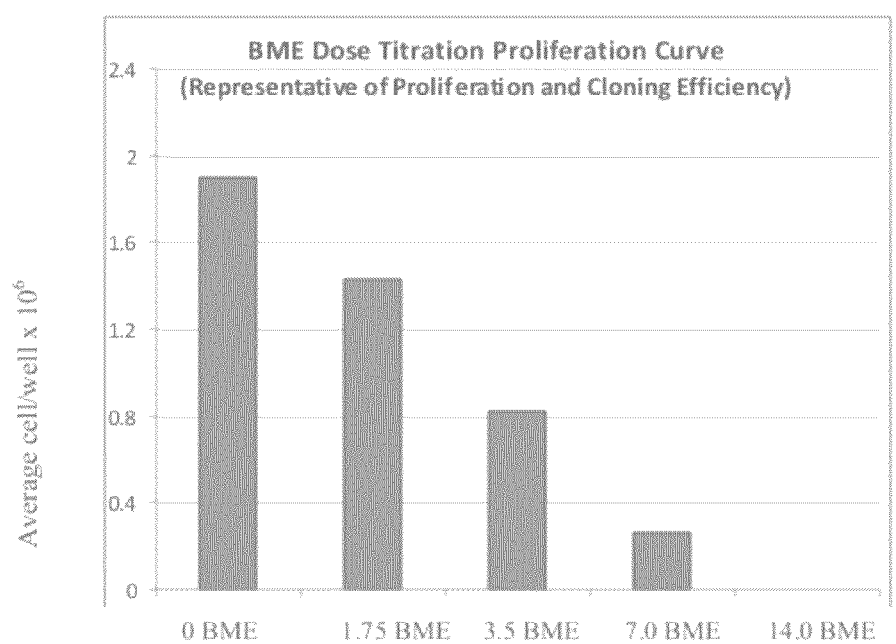
Figure 15C:
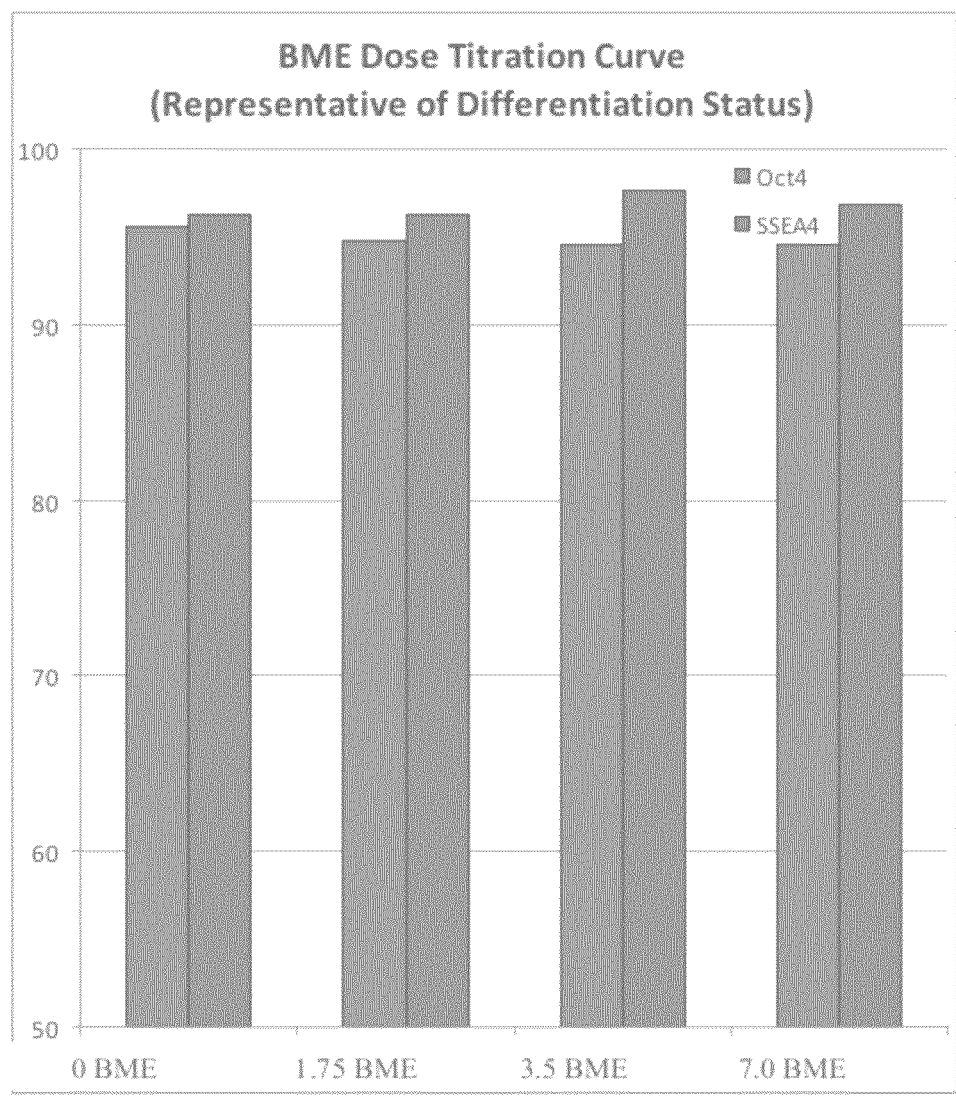

TeSR1 as defined in Table 1 includes BME (i.e., 2-mercaptothanol). Generally, it is known that BME reduces disulfide bonds and acts as an antioxidant by scavenging hydroxyl radicals. When BME is added to cell culture medium it is generally believed to reduce the oxidative stress on cells in culture. To test the strict necessity for BME in TeSR1, we tested 5 doses of BME in modified TeSR1: 0, 1.75, 3.5, 7, and 14 µL BME/500 mL of total media (FIG. 15). Based on cell counts and pluripotency, 0 and 1.75 µL BME/500 mL of total media yielded large increases in cloning efficiency of the cells (FIG. 15b). These data confirm that it is feasible and in some instances advantageous to culture pluripotent stem cells in TeSR1 in the absence of BME.

Figure 16A:
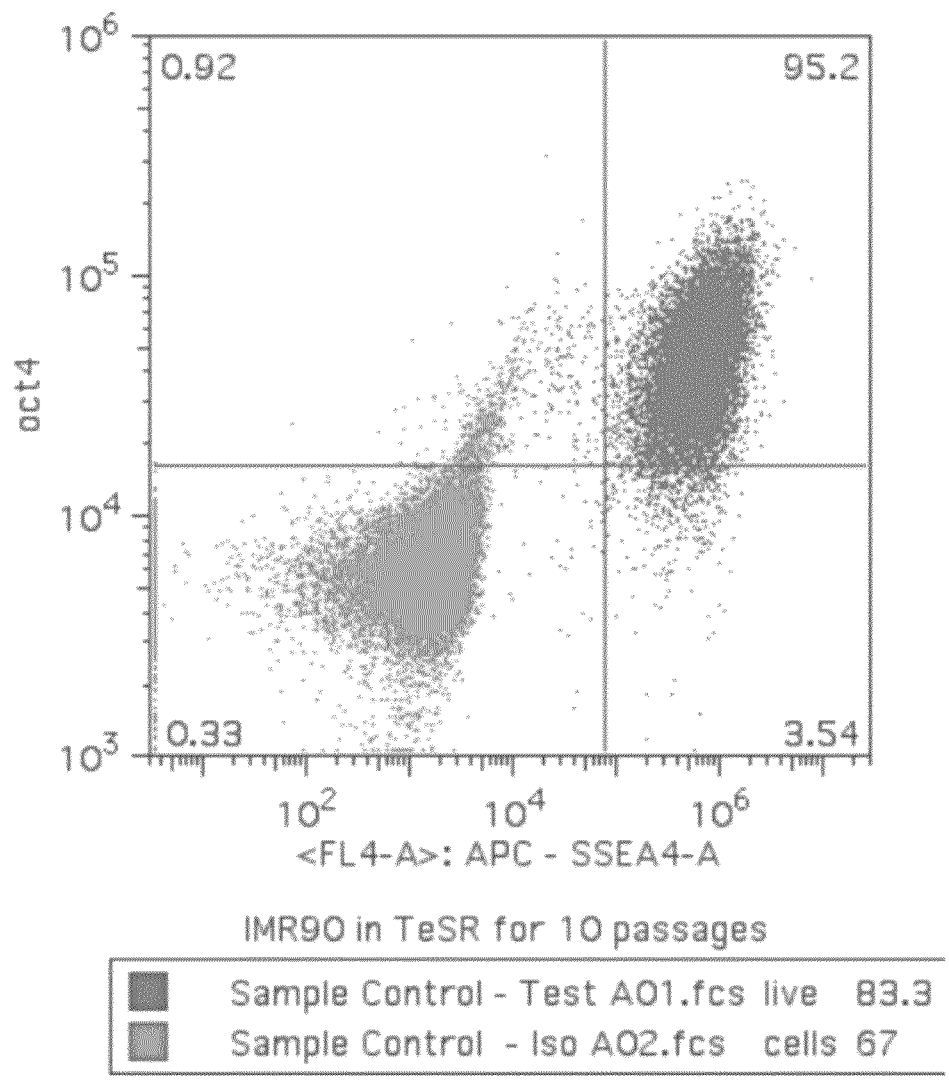
FIG. 16 illustrates the TeSR1 medium can also be used to culture and maintain iPS cells. Here pluripotent cells were generated from two iPS cell lines, each having gone through at least 10 passages in modified TeSR1 medium. (A) Flow cytometry data indicates that the iPS cell line IMR90, cultured for at least 10 passages in mTeSR1, maintained greater than 95% Oct-4 positive cells. (B) flow cytometry data indicates that the vector-free iPS cell line iPS-DF-19-9, cultured for at least 16 passages in mTeSR1, maintained more than 98% Oct-4 positive cells.
Figure 16B:
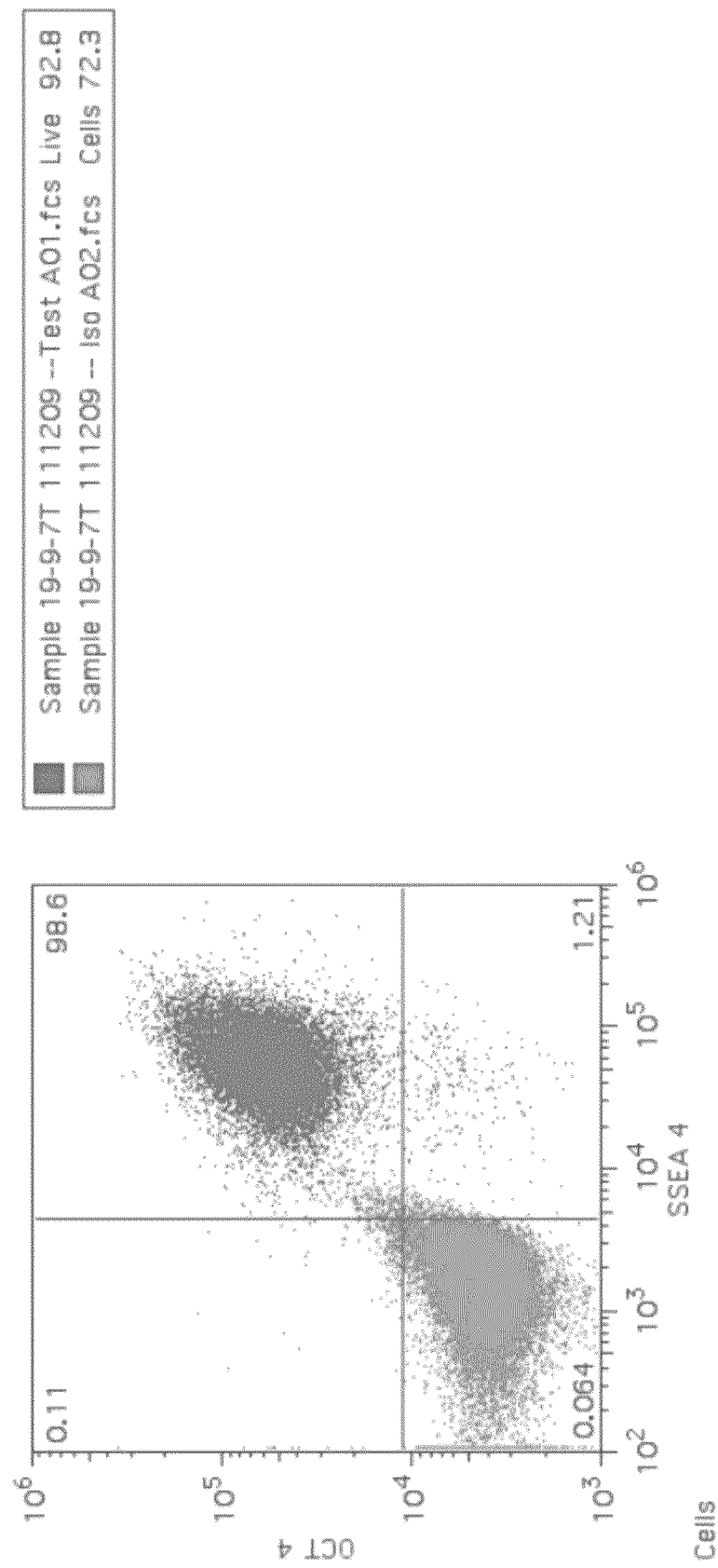

To confirm that the TeSR1 medium supports culture of non-embryonic pluripotent stem cells in an undifferentiated state, two iPS cells lines were cultured in modified TeSR1 (FIG. 16). The iPS cell line IMR90 (Yu et al., *Science* 2007; and provided by WISC Bank) was cultured for at least 10 passages in mTeSR1. Through 10 passages IMR90 maintained greater than 95% Oct-4 positive cells (FIG. 16a). The vector-free iPS cell line iPS-DF-19-9 (Yu et al., 2009 *Science*; also provided by WISC Bank) was cultured for at least 16 passages in mTeSR1. iPS-DF-19-9 maintained more than 98% Oct-4 positive cells, through 16 passages (FIG. 16B).

Recently, other research groups have also confirmed that the TeSR1 medium supports cell culture, maintenance and derivation of iPS cells. For example, Sun N, et al. reports the feeder-free derivation of induced pluripotent stem cells from adult human adipose stem cells with mTeSR1 hES growth medium available through StemCell Technologies located in Vancouver, BC, Canada. (Sun N, et al. *PNAS* 106(37), 15720-15725 (2009), incorporated by reference here in its entirety). Likewise, Chan E M, et al. have used mTeSR1 medium to derive fully reprogrammed iPS cells on Matrigel™ and shown that live cell imaging can distinguish bona fide human iPS cells from partially reprogrammed cells (Chan et al. *Nat. Biotech* 2009 Nov. 27 (11):1033-7, incorporated by reference here in its entirety). Collectively, these results indicate that the TeSR1 defined medium can support cell culture maintenance and derivation of pluripotent stem cells derived from somatic cells.

As described above, mTeSR1 and the original TeSR1 have the same function and are chemically similar. The main difference is that TeSR1 medium contains HSA, which is very expensive, and the mTeSR medium contains bovine serum albumin (BSA), which is more commercially economical. Because HSA is expensive to obtain, the inventors routinely use BSA as a less costly substitute. Although the species source of the albumin is different, BSA in the TeSR medium (mTeSR1) functions the same as its humanized counterpart, TeSR1 medium, which contains HSA. It is important to note that this humanized version of TeSR has been renamed and is currently marketed as TeSR2 by Stem Cell Technologies (Vancouver, BC, Canada).

It has been suggested that prior ES cell cultures are less than optimal because of the presence of Neu5Gc, a sialic acid not made by humans, contaminating human ES cells. Accordingly, to determine whether Neu5Gc could be eliminated from existing human ES cell lines, H9 cells were grown under three different conditions, 1) conditioned medium on Matrigel, 42 passages 2) TeSR1 on Matrigel, 16 passages and 3) TeSR1 on human matrix, 5 passages. Approximately $2\times10^7$ cells from each condition were collected and purified for analysis employing methods similar to those described previously (see Bardor, M. et al. *J Biol Chem* 280, 4228-4237; 2005). The purified sialic acids were derivatized with DMB (1,2-diamino-4,5-methylenedioxybenzene dihydrochloride) (Dojindo) to take advantage of previously described detection methods via liquid chromatography-mass spectrometry (LC-MS). The inventors employed a Surveyor HPLC in-line with a LCQ DECA XP Plus ion trap mass spectrometer (Thermo-Electron). The Genesis C18, 120 angstrom, 4 micron particle size (Grace Vydac) column was packed in-house (250 micron by 100 mm). Sample elution was carried out by ramping a linear gradient from 14% to 20% organic (acetonitrile:methanol) in 0.1% aqueous formic acid over 10 minutes at a flow rate of 1 µl/min (all solvents: Burdick & Jackson: High Purity). Electrospray voltage of 3300V, 175° C. capillary temperature and a nitrogen sheath gas of 15 psi were employed. Data acquisition was set for a full scan MS followed by two sequential MS/MS acquisitions for the parent masses of the Neu5Ac and Neu5Gc (426 and 442 m/z) derivatized products. Reconstructed ion chromatograms were plotted for the principle MS/MS daughter ions for Neu5Ac and Neu5Gc at 408 m/z and 424 m/z respectively. Conditions for derivatization and LC-MS analysis were established using commercially purchased standards of Neu5Ac and Neu5Gc (Sigma-Aldrich).

The inventors found that Neu5Gc was present on human ES cells cultured in fibroblast conditioned medium. A reduced but detectable amount of Neu5Gc was found on cells cultured in TeSR1 on Matrigel. However, no Neu5Gc was detected on ES cells cultured in TeSR1 using the four human matrix components. These data are illustrated in FIG. 12. Thus, human pluripotent stem cells cultured on TeSR1 and on a matrix of human proteins do not exhibit the non-human sialic acid residues found on cells cultured on murine feeder cells.

This medium has also proven capable of supporting the initiation of new lines of human pluripotent stem cells. The derivation process for new lines can be a difficult test for medium formulations, but the use of the defined medium makes it possible to create new lines of human pluripotent stem cells which have not been exposed to non-human animal proteins or matrices, and have never been exposed to feeder cells or medium in which feeder cells were cultured. This is believed to be a novel and unexpected achievement.

This work was undertaken only after obtaining institutional review board approval and informed consent from donors (HSC Protocol #2000-434). Frozen human pre-embryos that were fertilized for fertility treatment but were in excess of clinic need were thawed for the purpose of deriving new human pluripotent stem cell lines. Using commercially available sequential embryo culture media (Vitrolife—GIII Series) supplemented with 5% Serum Protein Substitute (SPS: Cooper Surgical), the frozen/thawed embryos were cultured for seven days in 10 μL drops under oil at 37° C. and 5% $O_2$/10% $CO_2$/85% $N_2$. After removal of the zona pellucida with pronase, the inner cell mass (ICM) of five human blastocysts were isolated by immunosurgery (Softer and Knowles, 1975, *Proc. Natl. Acad. Sci. USA*, 72:5099-5102) or as cultured whole mounts (Evans and Kaufman, 1981, *Nature*, 292154-156) and plated in 4-well culture plates (Nunc) onto the defined medium TeSR1 with the defined humanized matrix, CVFL, as described above. Following an initial 48 hours of culture, the culture medium (TeSR1) was replaced on a daily basis. After 14 to 21 days, clumps of cells were mechanically isolated and replated onto fresh human matrix. Mechanical isolation was continued for the subsequent 2 to 3 passages after which colonies were passaged using 0.5 mg/ml dispase (Invitrogen). The new colonies were confirmed to be new lines of human pluripotent stem cells using standard cell line characterization techniques.

Figure 13:
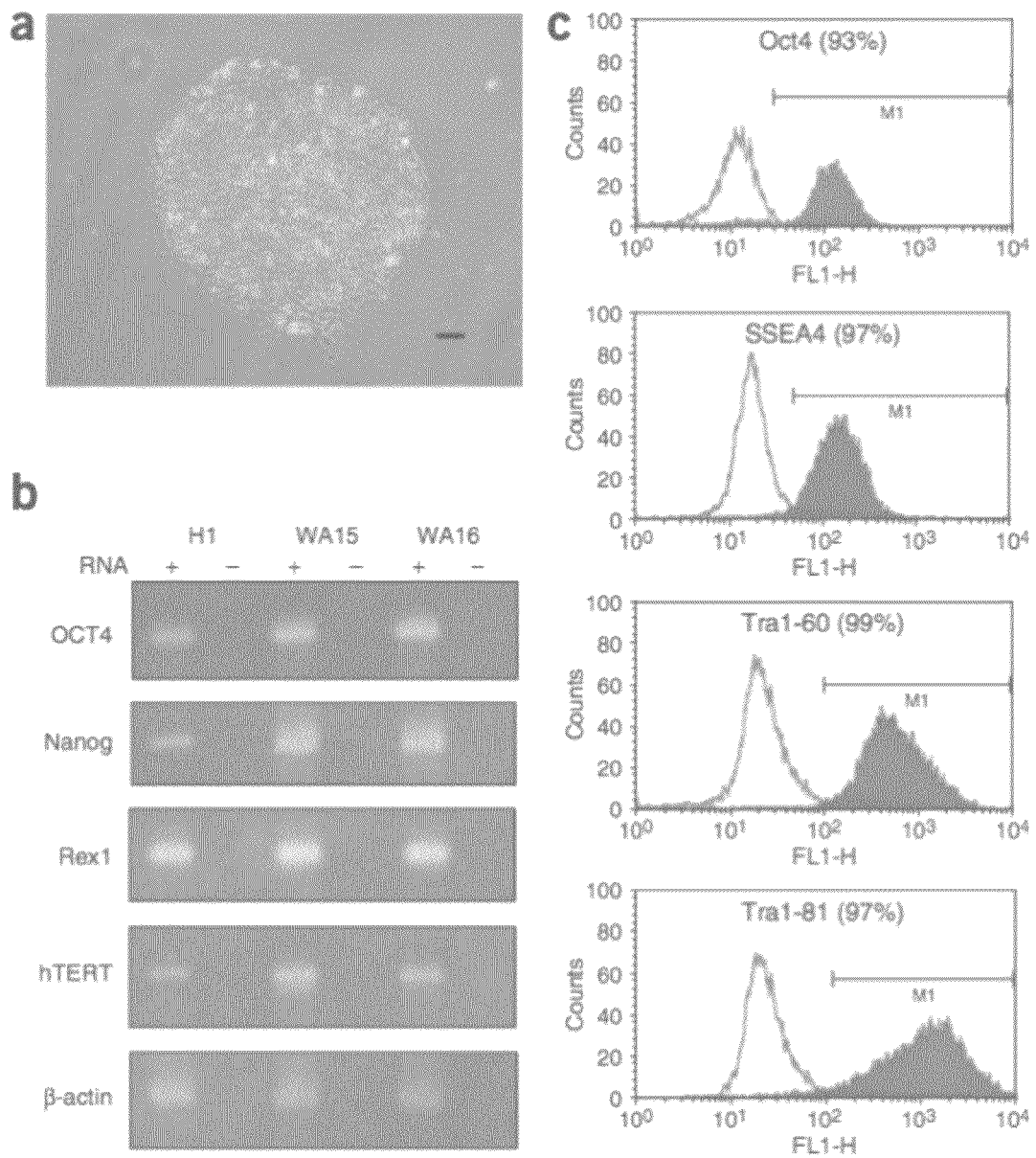
FIG. 13 shows representative morphology, RT-PCR and FACS analysis of human ES cells derived and maintained in defined, feeder-independent culture conditions: (a) WA 16 cells maintained in TeSR1 on human matrix components for 16 passages were photographed at 4× magnification using phase contrast microscopy (scale bar, 100 µm); (b) RT-PCR analysis of total RNA isolated from control cells (H1) or newly derived cell lines (WA15 and WA16), primer sets for pluripotency markers (Oct-4, Nanog, Rex1, hTERT) and a housekeeping gene (β-actin) were analyzed with (+) or without (−) RNA; and (c) WA15 cells were FACS analyzed after 18 passages for internal (Oct-4) or cell surface (SSEA-4, Tra 1-60, Tra 1-81) markers. Percentage of positive cells is listed in parentheses.

Using TeSR1 medium on the four human matrix components, CVFL, two new human ES cell lines (WA15 and WA16; FIG. 13) were derived from 5 cultured blastocysts. Both human ES cell lines have now been continuously in culture for more than 7 months. Analysis of these lines by fluorescence-activated cell sorting (FACS) and RT-PCR demonstrated that they express markers characteristic of human ES cells (FIG. 13), and both cell lines formed teratomas when injected into severe combined immunodeficient-beige mice.

FACS analysis was performed by first removing the cells from the culture dish with Trypsin/EDTA (Invitrogen) containing 2% chick serum (ICN) for 10 minutes at 37° C. and resuspended in 1 ml fluorescence activated cell sorting (FACS) buffer [PBS –/–(Invitrogen) containing 0.1% sodium azide (Sigma) and 2% fetal bovine serum (Gibco)]. Cells to be probed for the internal marker Oct-4 were fixed with 0.1% paraformaldehyde (Electron Microscopy Sciences) for 10 min. at 37° C. then permeabilized with 90% methanol (Fisher Scientific) for 30 min on ice. 1-5×$10^5$ fixed (Oct-4) or live (SSEA-4, Tra 1-60 or Tra 1-81) cells were then probed for 30 min at room temperature with a 1:100 dilution of the specific monoclonal antibody or an appropriate isotype control antibody (Santa Cruz Biotechnology, Inc.) in FACS buffer (+0.1% Triton-X100 for fixed cells). Cells were then washed and probed in FACS buffer (+0.5% Triton-X100 for fixed cells) with 1:1000 dilution of an Alexaflour anti-mouse secondary antibody (Invitrogen) for 30 min in the dark at room temperature. Cells with the EGFP-Oct-4 knock-in construct were collected and analyzed directly. Cell were washed in FACS Buffer, and sorted using a FACSCalibur flow cytometer (Becton Dickinson). Acquisition was set for 10,000 events per sample. Dead cells were excluded from analysis by staining with propidium iodide (Invitrogen). Data were analyzed with CellQuest 3.0 software (Becton Dickinson). All treatments were performed in duplicate. Multiple replicates were performed for each experiment.

RT-PCR was performed with previously described gene-specific primers on 100 ng of total RNA per reaction using an OneStep RT-PCR Kit (Qiagen) following manufacturer's recommendations. RNA concentrations were measured by UV absorption with a SmartSpec 3000 spectrophotometer (Bio-Rad). H1 cells were cultured in conditioned-medium on Matrigel for 32 passages, the WA15 and WA16 cells were cultured in TeSR1 on human matrix for 9 and 10 passages respectively. Transcripts were visualized on ethidium bromide stained agarose gels.

Figure 14A:
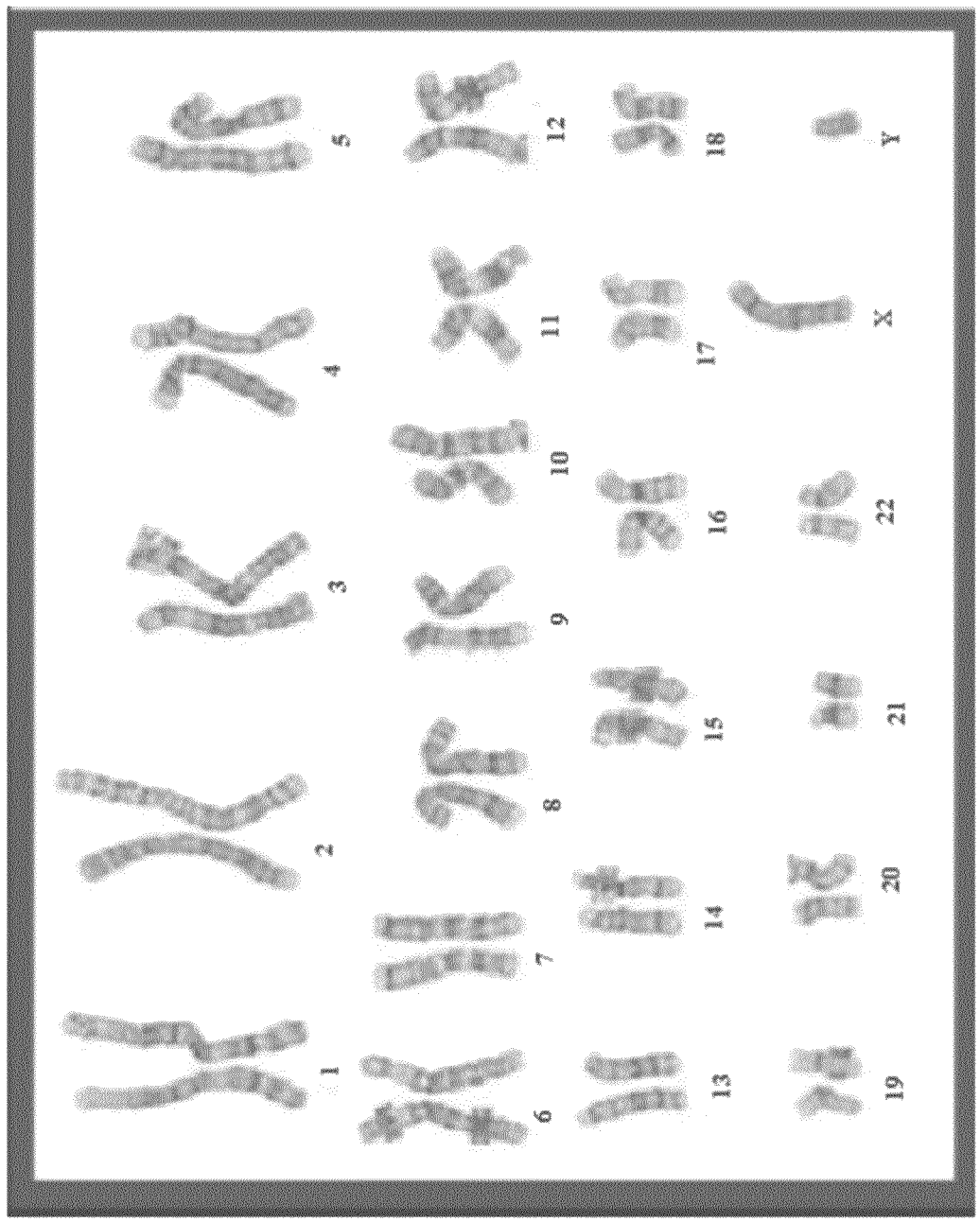
FIGS. 14A-B illustrate the karyotype of new human ES cell lines. Human ES cells derived and maintained in TeSR1 on human matrix components for 5 months (FIG. 14A) were subjected to cytogenetic analysis using G-banding (FIG. 14B); twenty metaphase cells from each of the cell lines were evaluated: (a) a normal 46XY karyotype was observed for all WA15 cells, while (b) all 20 WA16 cells demonstrated a 47XXY karyotype.
Figure 14B:
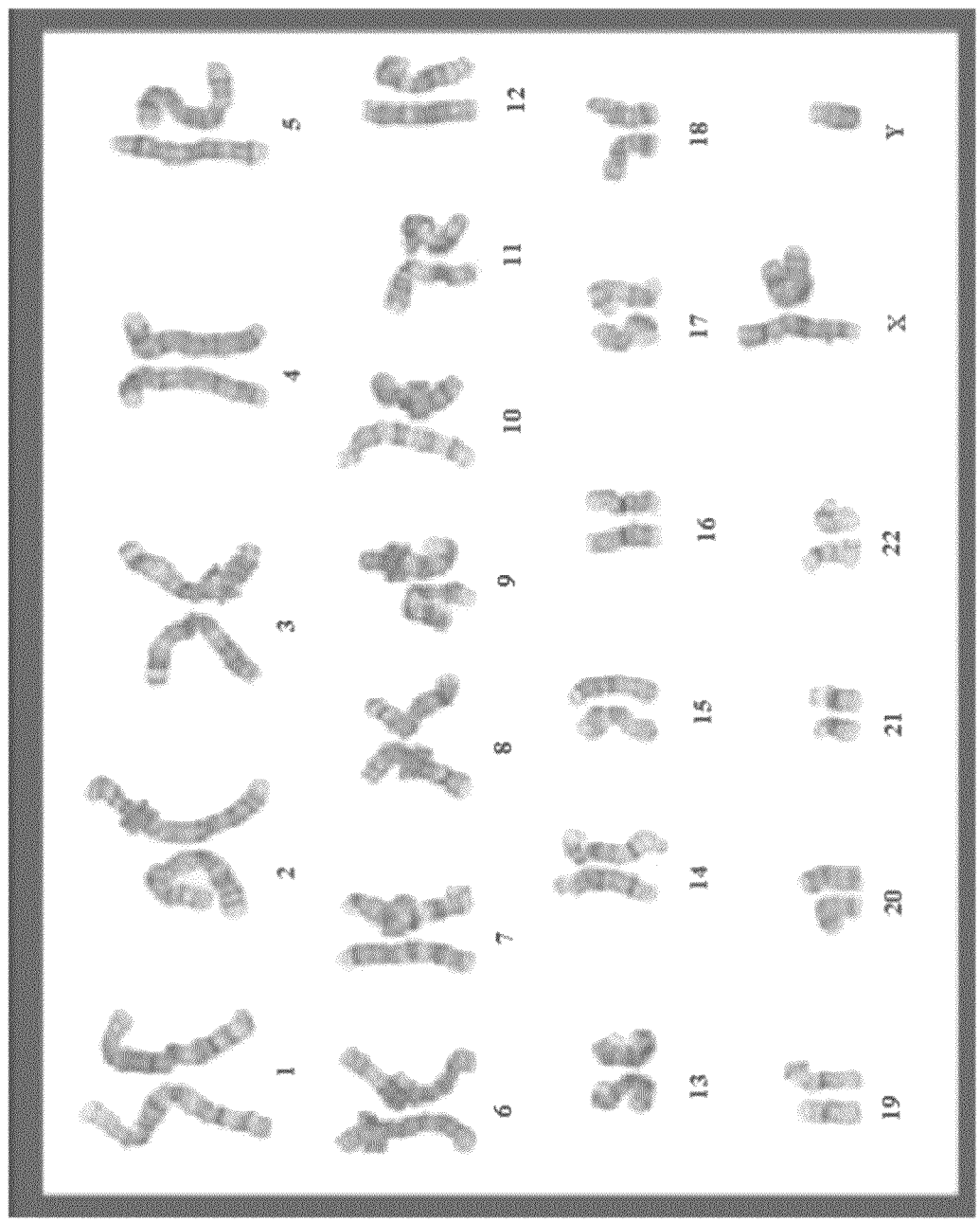

For each cell line, cytogenetic analysis was performed on 20 metaphase cells using G-banding. For long term cell cultures (H9, 21 passages in TeSR1) and newly derived cell lines (WA15 and WA16, 10 passages in culture), fluorescence in situ hybridization (FISH) was also performed on interphase nuclei using probes specific for the TEL gene on chromosome 12 and the Her-2/neu gene on chromosome 17. Two hundred cells were examined from each cell line. Trisomy 12 and/or 17, commonly reported in cultured human ES cells, was not detected in long term cultures of established cell lines or initial (4 months) cultures of newly derived cell lines. After four months in culture, WA16 was XXY (Klinefelter syndrome) and WA15 was karyotypically normal (XY; see FIG. 14). Klinefelter syndrome is the most common human chromosomal abnormality, suggesting that this abnormality may have been present in the embryo itself rather than an artifact introduced by the process of initiating the stem cell culture. After 7 months in culture, WA16 maintained its initial karyotype, but WA15 became trisomic for chromosome 12.

In summary, TeSR1 containing all five factors (bFGF, LiCl, GABA, PA and TGFβ) is sufficient to support feeder-independent human pluripotent stem cell culture as well as or better than fibroblast-conditioned medium, and remarkably, these factors do not overlap with the factors demonstrated to sustain mouse ES cells in defined conditions (Ying, Q. L. et al. *Cell* 115, 281-292 (2003)). Three of the factors present in TeSR1 (bFGF, TGFβ and LiCl) are believed to stimulate signaling pathways previously highlighted in human ES cell culture publications (see Xu, C. et al. *Stem Cells* 23, 315-323 (2005); Amit, M. et al. *J. Biol. Reprod.* 70, 837-845 (2004); and Sato, N. et al., *Nat. Med.* 10, 55-63 (2004)).

We initially tested GABA because microarray results indicated increased expression of the GABA-A receptor P-3 subunit by human ES cells (see Sperger, J. M. et al. *Proc. Natl. Acad. Sci. USA* 100, 13350-13355 (2003)). GABA is an inhibitory neurotransmitter of the central nervous system, and is reported to stimulate proliferation of both neural and non-neural tissues (see Watanabe, M., et al. *Int. Rev. Cytol.* 213, 1-417 (2002)). We tested pipecolic acid as it can enhance GABA-A receptor responses (see Takahama, K. et al. *Neuropharmacology* 25, 339-342 (1986)).

Unlike previous human pluripotent stem cell culture media that included proprietary, poorly defined serum components with undisclosed formulations, all TeSR1 components are disclosed, and thus should serve as a starting point for further optimization by other investigators. One area requiring improvement is the matrix, as the purified human matrix components are expensive and provide a potential route of contamination by human pathogens. Human serum albumin is the only component in the TeSR1 medium itself that is not fully defined, and it is possible that components that co-purify with it influence human pluripotent stem cells. Human serum albumin is routinely used for embryo culture during in vitro fertilization procedures, so its inclusion in TeSR1 does not qualitatively change the risk of introducing pathogens to the pluripotent stem cells, but clearly the replacement of this component by cloned materials would be desirable.

The new human ES cell line WA15 was initially normal, but converted to trisomy 12 between 4 and 7 months of culture. The emergence of this abnormal karyotype could be associated with the enzymatic dissociation used to passage the cells. Trisomy 12 in human ES cells has been reported previously (see Draper, J. S. et al. *Nat. Biotechnol.* 22, 53-54; 2004), and in our hands, has often been associated with clonal events. Human pluripotent stem cells clone at a poor efficiency (1%) and enzymatic methods of dissociation can result in a significant number of individualized cells. There is, therefore, significant selective pressure for karyotypic changes that increase cloning efficiency of the cells. Mechanical methods of passaging the cells that result in uniform clump size or improved cloning efficiencies could significantly reduce these selective pressures. Clearly, a better understanding of the rate of genetic change and the selective pressures that allow those changes to dominate a culture will be critical to any therapeutic application of human pluripotent stem cells.

Human pluripotent stem cell lines derived in defined conditions would be more directly applicable to clinical use than are cell lines derived in the presence of animal products. All of the human pluripotent stem cell lines currently approved for federal funding in the United States were derived on mouse feeder layers and were exposed to a variety of other poorly defined animal products. Derivation and culture in serum-free, animal product-free, feeder-independent conditions mean that new human pluripotent stem cell lines could be qualitatively different from the original lines, enabling increased clinical uses.

The disclosure of every patent, patent application, and publication cited herein is hereby incorporated by reference here in its entirety.

Although the foregoing invention has been described in some detail by way of illustration and example for purposes of clarity of understanding, it is understood that certain adaptations of the invention are a matter of routine optimization for those skilled in the art, and can be implemented without departing from the spirit of the invention, or the scope of the appended claims.

TABLE 1

| Complete Formulation for TeSR1 Medium | |
|---|---|
| | mM |
| INORGANIC SALTS | |
| Calcium chloride (Anhydrous) | 8.24E−01 |
| HEPES | 1.18E+01 |
| Lithium Chloride (LiCl) | 9.80E−01 |
| Magnesium chloride (Anhydrous) | 2.37E−01 |
| Magnesium Sulfate (MgSO4) | 3.19E−01 |
| Potassium chloride (KCl) | 3.26E+00 |
| Sodium bicarbonate (NaHCO3) | 1.80E+01 |
| Sodium chloride (NaCl) | 9.46E+01 |
| Sodium phosphate, dibas (Anhydrous) | 3.92E−01 |
| Sodium phosphate, mono. (NaH2PO4—H2O) | 3.55E−01 |
| TRACE MINERALS | |
| Ferric Nitrate (Fe(NO3)3—9H2O) | 9.71E−05 |
| Ferric sulfate (FeSO4—7H2O) | 1.18E−03 |
| Cupric sulfate (CuSO4—5H2O) | 4.08E−06 |
| Zinc sulfate (ZnSO4—7H2O) | 1.18E−03 |
| Ammonium Metavanadate NH4VO3 | 1.09E−05 |
| Mangenous Sulfate Mn SO4 H2O | 1.97E−06 |
| NiSO4 6H2O | 9.70E−07 |
| Selenium | 1.77E−04 |
| Sodium Meta Silicate Na2SiO3 9H2O | 9.66E−04 |
| SnCl2 | 1.24E−06 |
| Molybdic Acid, Ammonium salt | 1.97E−06 |
| CdCl2 | 1.22E−05 |
| CrCl3 | 1.98E−06 |
| AgNO3 | 9.81E−07 |
| AlCl3 6H2O | 4.87E−06 |
| Ba (C2H3O2)2 | 9.79E−06 |
| CoCl2 6H2O | 9.81E−06 |
| GeO2 | 4.97E−06 |
| KBr | 9.89E−07 |
| KI | 1.00E−06 |
| NaF | 9.83E−05 |
| RbCl | 9.81E−06 |
| ZrOCl2 8H2O | 9.80E−06 |
| ENERGY SUBSTRATES | |
| D-Glucose | 1.37E+01 |
| Sodium Pyruvate | 3.92E−01 |
| LIPIDS | |
| Linoleic Acid | 1.88E−04 |
| Lipoic Acid | 4.00E−04 |
| Arachidonic Acid | 1.29E−05 |
| Cholesterol | 1.12E−03 |
| DL-alpha tocopherol-acetate | 2.90E−04 |
| Linolenic Acid | 6.99E−05 |
| Myristic Acid | 8.59E−05 |
| Oleic Acid | 6.94E−05 |
| Palmitic Acid | 7.65E−05 |
| Palmitoleic acid | 7.71E−05 |
| Stearic Acid | 6.89E−05 |
| AMINO ACIDS | |
| L-Alanine | 1.37E−01 |
| L-Arginine hydrochloride | 5.48E−01 |
| L-Asparagine-H2O | 1.37E−01 |
| L-Aspartic acid | 1.37E−01 |
| L-Cysteine-HCl—H2O | 7.83E−02 |
| L-Cystine 2HCl | 7.83E−02 |
| L-Glutamic acid | 1.37E−01 |
| L-Glutamine | 2.94E+00 |
| Glycine | 2.94E−01 |
| L-Histidine-HCl—H2O | 1.18E−01 |
| L-Isoleucine | 3.26E−01 |
| L-Leucine | 3.54E−01 |
| L-Lysine hydrochloride | 3.91E−01 |
| L-Methionine | 9.06E−02 |
| L-Phenylalanine | 1.69E−01 |
| L-Proline | 2.16E−01 |
| L-Serine | 2.94E−01 |
| L-Threonine | 3.52E−01 |
| L-Tryptophan | 3.46E−02 |
| L-Tyrosine 2Na 2H2O | 1.68E−01 |
| L-Valine | 3.55E−01 |
| VITAMINS | |
| Ascorbic acid | 2.53E−01 |
| Biotin | 1.12E−05 |
| B12 | 3.94E−04 |
| Choline chloride | 5.03E−02 |

TABLE 1-continued

Complete Formulation for TeSR1 Medium

| | mM |
|---|---|
| D-Calcium pantothenate | 3.69E−03 |
| Folic acid | 4.71E−03 |
| i-Inositol | 5.49E−02 |
| Niacinamide | 1.30E−02 |
| Pyridoxine hydrochloride | 7.62E−03 |
| Riboflavin | 4.56E−04 |
| Thiamine hydrochloride | 2.42E−02 |
| GROWTH FACTORS/PROTEIN | |
| GABA | 9.79E−01 |
| Pipecolic Acid | 9.84E−04 |
| bFGF | 5.77E−06 |
| TGF beta 1 | 2.35E−08 |
| Human Insulin | 3.92E−03 |
| Human Holo-Transferrin | 1.37E−04 |
| Human Serum Albumin | 1.95E−01 |
| Glutathione (reduced) | 6.38E−03 |
| OTHER COMPONENTS | |
| Hypoxanthine Na | 1.18E−02 |
| Phenol red | 1.69E−02 |
| Putrescine-2HCl | 3.95E−04 |
| Thymidine | 1.18E−03 |
| 2-mercaptoethanol | 9.80E−02 |
| Pluronic F-68 | 2.33E−02 |
| Tween 80 | 3.29E−04 |

RELATED PUBLICATIONS

1. Puck, T. T. & Marcus, P. I. *Proc. Natl. Acad. Sci. USA* 4, 432-437 (1955).
2. Thomson, J. A. et al. *Science* 282, 1145-1147 (1998).
3. Ying, Q. L. et al. *Cell* 115, 281-292 (2003).
4. Xu, R. H. et al. *Nat. Biotechnol.* 20, 1261-1264 (2002).
5. Xu, R. H. et al. *Nat. Methods* 2, 185-190 (2005).
6. Amit, M. et al. *Dev. Biol.* 227, 271-278 (2000).
7. Klimanskaya, I. et al. *Lancet* 365, 1636-1641 (2005).
8. Xu, C. et al. *Stem Cells* 23, 315-323 (2005).
9. Martin, M. J. et al. *Nat. Med.* 11, 228-232 (2005).
10. Sperger, J. M. et al. *Proc. Natl. Acad. Sci. USA* 100, 13350-13355 (2003).
11. Amit, M. et al. *J. Biol. Reprod.* 70, 837-845 (2004).
12. Sato, N. et al., *Nat. Med.* 10, 55-63 (2004).
13. Watanabe, M., et al. *Int. Rev. Cytol.* 213, 1-417 (2002).
14. Takahama, K. et al. *Neuropharmacology* 25, 339-342 (1986).
15. Draper, J. S. et al. *Nat. Biotechnol.* 22, 53-54 (2004).
16. Xu, C. et al. *Nature Biotechnology* 19, 971-974 (2001).
17. Zwaka, T. P. & Thomson, J. A. *Nat Biotechnol* 21, 319-321. (2003).
18. Bardor, M. et al. *J Biol Chem* 280, 4228-4237 (2005).
19. Hara, S. et al. *Anal Biochem* 179, 162-166 (1989).
20. Klein, A. et al. *Glycobiology* 7, 421-432 (1997).
21. Ludwig T. E. et al. *Nat. Biotech.* 24(2), 185-187 (2006).
22. Yu J. et al. *Science,* 318(5858), 1917-1920 (2007).
23. Ludwig T. E. et al. *Nature Methods,* 3, 637-646 (2006) and Supplementary Materials.
24. Yu J. et al. *Science,* 324(5928), 797-801 (2009).
25. Park I H. et al. *Nature,* 451(7175), 141-6 (2008).
26. Chan E M, et al. *Nat. Biotech,* 27(11), 1033-7 (2009) and Supplementary Materials.
27. Sun N, et al. *PNAS* 106(37), 15720-15725 (2009).
28. U.S. Pat. No. 7,592,175.
29. U.S. Pat. No. 7,449,334.
30. U.S. Pat. No. 7,442,548.
31. U.S. Pat. No. 7,005,252.
32. U.S. Pat. No. 7,217,569.
33. U.S. Pat. No. 7,455,983.
34. U.S. Pat. No. 7,413,902.
35. U.S. Pat. No. 7,410,798.
36. U.S. Pat. No. 7,297,539.
37. U.S. Pat. No. 6,800,480.
38. Mallon et al., *International Journal of Biochemistry and Cell Biology*, Vol. 38, 1063-1075 (2006).

We claim:

1. A medium comprising salts, vitamins, amino acids, glucose, albumin, minerals, lipids, a transferrin or a transferrin substitute, insulin or an insulin substitute, a fibroblast growth factor, and at least one member selected from gamma-aminobutyric acid, pipecolic acid and lithium, and optionally transforming growth factor beta, in sufficient amounts to maintain stem cells grown in the medium in an undifferentiated state through multiple culture passages.

2. A medium comprising salts, vitamins, amino acids, glucose, albumin, minerals, lipids, a transferrin or a transferrin substitute, insulin or an insulin substitute, a fibroblast growth factor, and at least two members selected from gamma-aminobutyric acid, pipecolic acid and lithium, and optionally transforming growth factor beta, in sufficient amounts to maintain stem cells grown in the medium in an undifferentiated state through multiple culture passages.

3. A medium comprising salts, vitamins, amino acids, glucose, albumin, minerals, lipids, a transferrin or a transferrin substitute, insulin or an insulin substitute, a fibroblast growth factor, gamma-aminobutyric acid, pipecolic acid and lithium, and optionally transforming growth factor beta, in sufficient amounts to maintain stem cells grown in the medium in an undifferentiated state through multiple culture passages.

4. The medium of claim 1, 2 or 3, wherein the insulin and transferrin are recombinant proteins.

5. The medium of claim 1, 2 or 3, wherein the stem cells are primate pluripotent stem cells.

\* \* \* \* \*